US007696406B2

(12) United States Patent
Allison

(10) Patent No.: US 7,696,406 B2
(45) Date of Patent: Apr. 13, 2010

(54) EXPRESSION OF A RECOMBINANT TRANSGENE

(75) Inventor: Richard F. Allison, Leslie, MI (US)

(73) Assignee: Board of Trustees Operating Michigan State University, East Lansing, MI (US)

( * ) Notice: Subject to any disclaimer, the term of this patent is extended or adjusted under 35 U.S.C. 154(b) by 338 days.

(21) Appl. No.: 10/561,720

(22) PCT Filed: Jul. 2, 2004

(86) PCT No.: PCT/US2004/021451

§ 371 (c)(1),
(2), (4) Date: Dec. 22, 2005

(87) PCT Pub. No.: WO2005/019449

PCT Pub. Date: Mar. 3, 2005

(65) Prior Publication Data

US 2007/0136890 A1 Jun. 14, 2007

Related U.S. Application Data

(60) Provisional application No. 60/485,073, filed on Jul. 3, 2003.

(51) Int. Cl.
*C12N 15/82* (2006.01)
*C12N 15/87* (2006.01)
*A01H 1/00* (2006.01)
*C07H 21/04* (2006.01)

(52) U.S. Cl. ...................... 800/278; 800/288; 536/24.1; 536/23.72

(58) Field of Classification Search ...................... None
See application file for complete search history.

(56) References Cited

U.S. PATENT DOCUMENTS

| | | | | |
|---|---|---|---|---|
| 5,166,057 | A | 11/1992 | Palese et al. | |
| 5,578,473 | A | 11/1996 | Palese et al. | |
| 5,583,021 | A | 12/1996 | Dougherty et al. | |
| 5,766,882 | A | 6/1998 | Falkner et al. | |
| 5,840,520 | A | 11/1998 | Clarke et al. | |
| 5,854,037 | A | 12/1998 | Palese et al. | |
| 6,136,538 | A | 10/2000 | Olivo et al. | |
| 6,197,542 | B1 | 3/2001 | Van Haute et al. | |
| 6,270,958 | B1 | 8/2001 | Olivo et al. | |
| 6,326,480 | B1 | 12/2001 | Kovelman et al. | |
| 6,433,248 | B1 | 8/2002 | Lommel et al. | |
| 6,462,255 | B1 | 10/2002 | Turpen | |
| 6,479,291 | B2 | 11/2002 | Kumagai et al. | |
| 2002/0138873 | A1 | 9/2002 | Lewandowski et al. | |
| 2004/0055037 | A1* | 3/2004 | Gleba et al. | 800/280 |

FOREIGN PATENT DOCUMENTS

| | | | |
|---|---|---|---|
| WO | WO 00/78985 | | 12/2000 |
| WO | WO-02/12522 | A | 2/2002 |
| WO | WO-02/29068 | A | 4/2002 |
| WO | WO 03/023064 | | 3/2003 |

OTHER PUBLICATIONS

Teycheney et al. 2000, Journal of General Virology 81:1121-1126.*
Basso et al. 1994, Journal of General Virology 75:3157-3165.*
Toth, R. L., et al: “A novel strategy for the expression of foreign genes from plant virus vectors”, FEBS Letters, Elsevier Science Publishers, Amsterdam, NL, vol. 489, No. 2-3, Feb. 2, 2001, pp. 215-219, XP004248888; ISSN: 0014-5793.
Bonnal et al., IRESdb: the Internal Ribosome Entry Site database. Nucleic Acids Research 31(1):427-428 (2003).
Cornejo et al., Activity of a maize ubiquitin promoter in transgenic rice. Plant Molecular Biology 23:567-581 (1993).
Fitchen et al., Genetically Engineered Protection Against Viruses in Transgenic Plants. Annu. Rev. Microbiol. 47:739-63 (1993).
Gallie, Cap-Independent Translation Conferred by the 5' Leader of Tobacco Etch Virus Is Eukaryotic Initiation Factor 4G Dependent. Journal of Virology 75(24):12141-12152 (2001).
Greene et al., Deletions in the 3' Untranslated Region of Cowpea Chlorotic Mottle Virus Transgene Reduce Recovery of Recombinant Viruses in Transgenic Plants. Virology 225:231-234 (1996).
Greene et al., Recombination Between Viral RNA and Transgenic Plant Transcripts. Science 263:1423-1425 (1994).
Holtorf et al., Comparison of different constitutive and inducible promoters for the overexpression of transgenes in *Arabidopsis thaliana*. Plant Molecular Biology 29:637-646 (1995).
Ivanov et al., A Tobamovirus Genome That Contains an Internal Ribosome Entry Site Functional in Vitro. Virology 232:32-43 (1997).
Koh et al., Synergism of the 3'-Untranslated Region and an Internal Ribosome Entry Site Differentially Enhances the Translation of a Plant Virus Coat Protein. The Journal of Biological Chemistry 278(23): 20565-20573 (2003).
Lepetit et al., A plant histone gene promoter can direct both replication-dependent and -independent gene expression in transgenic plants. Mol Gen Genet 231:276-285 (1992).

(Continued)

*Primary Examiner*—Anne Marie Grunberg
*Assistant Examiner*—Li Zheng
(74) *Attorney, Agent, or Firm*—Harness, Dickey & Pierce, P.L.C.

(57) ABSTRACT

A system for expression of a heterologous polypeptide in a transgenic host cell is disclosed. The system is based upon a transgene comprising a eukaryotic promoter operably linked to a DNA sequence comprising, in the 5' to 3' direction, a DNA sequence complementary to a sequence encoding a heterologous polypeptide, a DNA sequence complementary to an internal ribosome entry site, and a DNA sequence corresponding to a 3' untranslated region of a positive strand single-stranded RNA virus. Following introduction of a stimulus, the host cell synthesizes an RNA molecule complementary to a recombinant RNA encoded by the transgene. The stimulus can be a positive strand single-stranded RNA virus or a nucleic acid thereof. Because the complement of the recombinant RNA comprises an internal ribosome entry site and a sequence encoding a heterologous polypeptide, the host cell can synthesize the heterologous polypeptide.

51 Claims, 6 Drawing Sheets

OTHER PUBLICATIONS

Mandel et al., Definition of a constitutive gene expression in plants: the translation initiation factor 4A gene as a model. Plant Molecular Biology 29:995-1004 (1995).

McElroy et al., Isolation of an Efficient Actin Promoter for Use in Rice Transformation. The Plant Cell 2:163-171 (1990).

Powell et al., Protection against tobacco mosaic virus in transgenic plants that express tobacco mosaic virus antisense RNA. Proc. Natl. Acad. Sci. USA 86:6949-6952 (1989).

Praz et al., The Eukaryotic Promoter Database, EPD: new entry types and links to gene expression data. Nucleic Acids Research 30(1):322-324 (2002).

Schenk et al., A promoter from sugarcane bacilliform badnavirus drives transgene expression in banana and other monocot and dicot plants. Plant Molecular Biology 39:1221-1230 (1999).

Strauss et al., Viruses and Human Disease. An Overview of the Replication Cycle of Viruses. Academic Press 24-25 (2002).

van Rossum et al., The 3' untranslated region of alfalfa mosaic virus RNA3 contains a core promoter for minus-strand RNA synthesis and an enhancer element. Journal of General Virology 78:3045-3049 (1997).

Verdaguer et al., Isolation and expression in transgenic tobacco and rice plants, of the cassava vein mosaic virus (CVMV) promoter. Plant Molecular Biology 31:1129-1139 (1996).

Wilmink et al., Activity of constitutive promoters in various species from the Liliaceae. Plant Molecular Biology 28:949-955 (1995).

Zaccomer et al., Transgenic plants that express genes including the 3' untranslated region of the turnip yellow mosaic virus (TYMV) genome are partially protecteed against TYMV infection. Gene 136:87-94 (1993).

Allison et al., Regeneration of a functional RNA virus genome by recombination between deletion mutants and requirement for cowpea chlorotic mottle virus 3a and coat genes for systemic infection, Proc. Natl. Acad. Sci. USA 87:1820-1824 (1990).

Hsue et al., A Bulged Stem-Loop Structure in the 3' Untranslated Region of the Genome of the Coronavirus Mouse Hepatitis Virus Is Essential for Replication, Journal of Virology 71(10):7567-7578 (1997).

Leuchtenberger et al., Conditional cell ablation by stringent tetracycline-dependent regulation of barnase in mammalian cells, Nucleic Acids Research 29(16):1-6 (2001).

Lin et al., The 3' Untranslated Region of Coronavirus RNA is Required for Subgenomic mRNA Transcription from a Defective Interfering RNA, Journal of Virology 70(10):7236-7240 (1996).

Lu et al., Poliovirus chimeras replicating under the translational control of genetic elements of hepatitis C virus reveal unusual properties of the internal ribosomal entry site of hepatitis C virus, Proc. Natl. Acad. Sci. USA 93:1412-1417 (1996).

Luckow et al., Efficient Generation of Infectious Recombinant Baculoviruses by Site-Specific Transposon-Mediated Insertion of Foreign Genes into a Baculovirus Genome Propogated in *Escherichia coli*, Journal of Virology 67(8):4566-4579 (1993).

Sanchez-Navarro et al., Engineering of Alfalfa mosaic virus RNA 3 into an expression vector, Archives of Virology 146:923-939 (2001).

Schneider et al., The Carboxy-Terminal Two-Thirds of the Cowpea Chlorotic Mottle Bromovirus Capsid Protein Is Incapable of Virion Formation yet Supports Systemic Movement, Journal of Virology 71(6):4862-4865 (1997).

Schuster et al., Secondary Structure of the 3' Terminus of Hepatitis C Virus Minus-Strand RNA, Journal of Virology 76(16):8058-8068 (2002).

Weber et al., Recent advances in retrovirus vector-mediated gene therapy: Teaching an old vector new tricks, Current Opinion in Molecular Therapeutics 3(5):439-453 (2001).

Wood et al., An internal ribosome binding site can be used to select for homologous recombinants at an immunoglobulin heavy-chain locus, Proc. Natl. Acad. Sci. USA 88:8006-8010 (1991).

Yu et al., Identification of cis-acting signals in the giardiavirus (GLV) genome required for expression of firefly luciferase in *Giardia lamblia*, RNA 2:824-834 (1996).

* cited by examiner

A. 5'—Promoter—α-coding—α-IRES—3'UTR→3'

B. 5'—α-coding—α-IRES—3'UTR→3'

C. 5'—α-3'UTR—IRES—coding→3'

Figure 5:
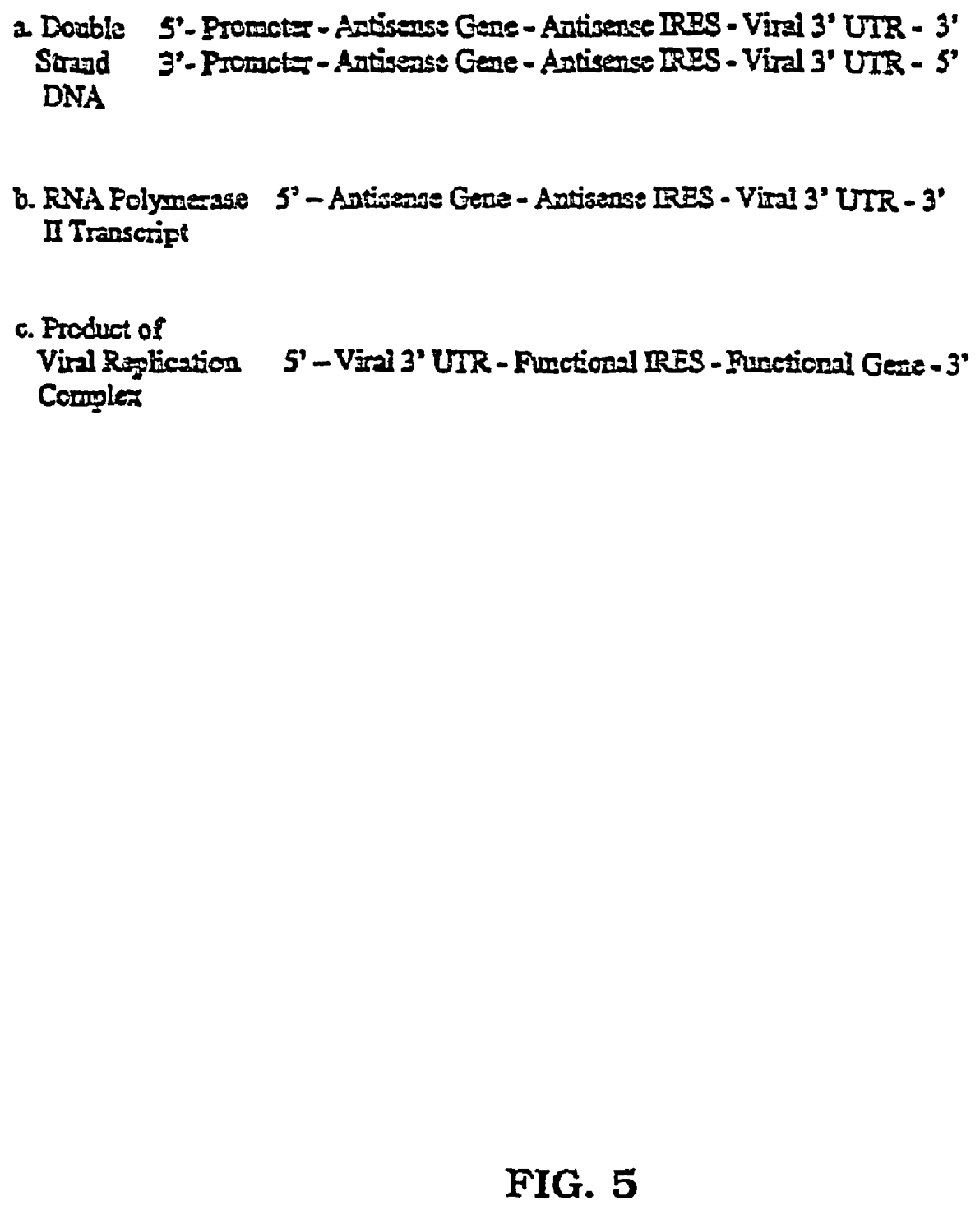

FIG. 1 a. Double Strand DNA
5'- Promoter - Antisense Gene - Antisense IRES - Viral 3' UTR - 3'
3'- Promoter - Antisense Gene - Antisense IRES - Viral 3' UTR - 5' b. RNA Polymerase II Transcript
5' – Antisense Gene - Antisense IRES - Viral 3' UTR - 3' c. Product of Viral Replication Complex
5' – Viral 3' UTR - Functional IRES - Functional Gene - 3'

FIG. 5 a.

DNA
5' - Promoter TTAAGG TACYYY* Viral 3' UTR – 3'
3' – Promoter AATTCC ATGXXX* Viral 3'UTR – 5' b.

RNA 5'- UUAAGG UACYYY* Viral 3' UTR – 3' c.

RNA 5' - Viral 3' UTR AAUUCC AUGXXX* - 3'

FIG. 6

SEQUENCE LISTING

```
<160> NUMBER OF SEQ ID NOS: 19

<210> SEQ ID NO 1
<211> LENGTH: 26
<212> TYPE: DNA
<213> ORGANISM: Cowpea chlorotic mottle virus

<400> SEQUENCE: 1

aagtggatcc cctcttgtgc ggctgc                                            26


<210> SEQ ID NO 2
<211> LENGTH: 16
<212> TYPE: DNA
<213> ORGANISM: Cowpea chlorotic mottle virus

<400> SEQUENCE: 2

actccaaaga gttctt                                                       16


<210> SEQ ID NO 3
<211> LENGTH: 835
<212> TYPE: DNA
<213> ORGANISM: Cauliflower mosaic virus

<400> SEQUENCE: 3

agattagcct tttcaatttc agaaagaatg ctaacccaca gatggttaga gaggcttacg      60

cagcaggtct catcaagacg atctacccga gcaataatct ccaggaaatc aaataccttc     120
```

-continued

```
ccaagaaggt taaagatgca gtcaaaagat tcaggactaa ctgcatcaag aacacagaga    180
aagatatatt tctcaagatc agaagtacta ttccagtatg gacgattcaa ggcttgcttc    240
acaaaccaag gcaagtaata gagattggag tctctaaaaa ggtagttccc actgaatcaa    300
aggccatgga gtcaaagatt caaatagagg acctaacaga actcgccgta aagactggcg    360
aacagttcat acagagtctc ttacgactca atgacaagaa gaaaatcttc gtcaacatgg    420
tggagcacga cacacttgtc tactccaaaa atatcaaaga tacagtctca gaagaccaaa    480
gggcaattga gacttttcaa caaagggtaa tatccggaaa cctcctcgga ttccattgcc    540
cagctatctg tcactttatt gtgaagatag tggaaaagga aggtggctcc tacaaatgcc    600
atcattgcga taaaggaaag gccatcgttg aagatgcctc tgccgacagt ggtcccaaag    660
atggaccccc acccacgagg agcatcgtgg aaaaagaaga cgttccaacc acgtcttcaa    720
agcaagtgga ttgatgtgat atctccactg acgtaaggga tgacgcacaa tcccactatc    780
cttcgcaaga cccttcctct atataaggaa gttcatttca tttggagaga acacg         835
```

<210> SEQ ID NO 4
<211> LENGTH: 581
<212> TYPE: DNA
<213> ORGANISM: Encephalomyocarditis virus

<400> SEQUENCE: 4

```
aattccgccc ctctccctcc cccccccta acgttactgg ccgaagccgc ttggaataag     60
gccggtgtgc gtttgtctat atgtgatttt ccaccatatt gccgtctttt ggcaatgtga    120
gggcccggaa acctggccct gtcttcttga cgagcattcc taggggtctt tcccctctcg    180
ccaaaggaat gcaaggtctg ttgaatgtcg tgaaggaagc agttcctctg gaagcttctt    240
gaagacaaac aacgtctgta gcgacccttt gcaggcagcg gaacccccca cctggcgaca    300
ggtgcctctg cggccaaaag ccacgtgtat aagatacacc tgcaaaggcg gcacaacccc    360
agtgccacgt tgtgagttgg atagttgtgg aaagagtcaa atggctctcc tcaagcgtat    420
tcaacaaggg gctgaaggat gcccagaagg taccccattg tatgggatct gatctggggc    480
ctcggtgcac atgctttaca tgtgtttagt cgaggttaaa aaacgtcta ggccccccga     540
accacgggga cgtggttttc ctttgaaaaa cacgatgata a                        581
```

<210> SEQ ID NO 5
<211> LENGTH: 581
<212> TYPE: RNA
<213> ORGANISM: Encephalomyocarditis virus

<400> SEQUENCE: 5

```
aauuccgccc cucucccucc cccccccua acguuacugg ccgaagccgc uuggaauaag     60
gccggugugc guuugucuau augugauuuu ccaccauauu gccgucuuuu ggcaauguga    120
gggcccggaa accuggcccu gucuucuuga cgagcauucc uaggggucuu uccccucucg    180
ccaaaggaau gcaaggucug uugaaugucg ugaaggaagc aguuccucug gaagcuucuu    240
gaagacaaac aacgucugua gcgacccuuu gcaggcagcg gaacccccca ccuggcgaca    300
ggugccucug cggccaaaag ccacguguau aagauacacc ugcaaaggcg gcacaacccc    360
agugccacgu ugugaguugg auaguugugg aaagagucaa auggcucucc ucaagcguau    420
ucaacaaggg gcugaaggau gcccagaagg uaccccauug uaugggaucu gaucuggggc    480
cucggugcac augcuuuaca uguguuuagu cgagguuaaa aaacgucua ggccccccga     540
```

-continued accacgggga cgugguuuuc cuuugaaaaa cacgaugaua a 581

<210> SEQ ID NO 6
<211> LENGTH: 581
<212> TYPE: DNA
<213> ORGANISM: Encephalomyocarditis virus

<400> SEQUENCE: 6
ttatcatcgt gtttttcaaa ggaaaaccac gtccccgtgg ttcgggggc ctagacgttt 60 ttttaacctc gactaaacac atgtaaagca tgtgcaccga ggccccagat cagatcccat 120
acaatggggt accttctggg catccttcag ccccttgttg aatacgcttg aggagagcca 180
tttgactctt tccacaacta tccaactcac aacgtggcac tggggttgtg ccgcctttgc 240
aggtgtatct tatacacgtg gcttttggcc gcagaggcac ctgtcgccag gtgggggtt 300 ccgctgcctg caaagggtcg ctacagacgt tgtttgtctt caagaagctt ccagaggaac 360
tgcttccttc acgacattca acagaccttg cattcctttg gcgagagggg aaagacccct 420
aggaatgctc gtcaagaaga cagggccagg tttccgggcc ctcacattgc caaaagacgg 480
caatatggtg gaaaatcaca tatagacaaa cgcacaccgg ccttattcca agcggcttcg 540
gccagtaacg ttaggggggg gggagggaga ggggcggaat t 581

<210> SEQ ID NO 7
<211> LENGTH: 581
<212> TYPE: RNA
<213> ORGANISM: Encephalomyocarditis virus

<400> SEQUENCE: 7
uuaucaucgu guuuuucaaa ggaaaaccac guccccgugg uucgggggc cuagacguuu 60 uuuuaaccuc gacuaaacac auguaaagca ugugcaccga ggccccagau cagaucccau 120
acaauggggu accuucuggg cauccuucag ccccuuguug aauacgcuug aggagagcca 180
uuugacucuu uccacaacua uccaacucac aacguggcac ugggguugug ccgccuuugc 240
agguguaucu uauacacgug gcuuuuggcc gcagaggcac cugucgccag guggggguu 300 ccgcugccug caaagggucg cuacagacgu uguuugucuu caagaagcuu ccagaggaac 360
ugcuuccuuc acgacauuca acagaccuug cauuccuuug gcgagagggg aaagaccccu 420
aggaaugcuc gucaagaaga cagggccagg uuuccgggcc cucacauugc caaaagacgg 480
caauauggug gaaaaucaca uauagacaaa cgcacaccgg ccuuauucca agcggcuucg 540
gccaguaacg uuaggggggg gggagggaga ggggcggaau u 581

<210> SEQ ID NO 8
<211> LENGTH: 242
<212> TYPE: DNA
<213> ORGANISM: Cowpea chlorotic mottle virus

<400> SEQUENCE: 8
agtgcccgct gaagagcgtt acactagtgt ggcctacttg aaggctagtt ataaccgttt 60
ctttaaacgg taatcgttgt tgaaacgtct tccttttaca agaggattga gctgcccttg 120
ggttttactc cttgaaccct tcggaagaac tctttggagt tcgtaccagt acctcacata 180
gtgaggtaat aagactggtg ggcagcgcct agtcgaaaga ctaggtgatc tctaaggaga 240
cc 242

<210> SEQ ID NO 9
<211> LENGTH: 242

-continued

<212> TYPE: RNA
<213> ORGANISM: Cowpea chlorotic mottle virus

<400> SEQUENCE: 9
agugcccgcu gaagagcguu acacuagugu ggccuacuug aaggcuaguu auaaccguuu 60
cuuuaaacgg uaaucguugu ugaaacgucu uccuuuuaca agaggauuga gcugcccuug 120
gguuuuacuc cuugaacccu acggaagaac ucuuuggagu ucguaccagu accucacaua 180
gugagguaau aagacuggug ggcagcgccu agucgaaaga cuaggugaug ucuaaggaga 240
cc 242

<210> SEQ ID NO 10
<211> LENGTH: 242
<212> TYPE: DNA
<213> ORGANISM: Cowpea chlorotic mottle virus

<400> SEQUENCE: 10
ggtctcctta gagatcacct agtctttcga ctaggcgctg cccaccagtc ttattacctc 60
actatgtgag gtactggtac gaactccaaa gagttcttcc gaagggttca aggagtaaaa 120
cccaagggca gctcaatcct cttgtaaaag gaagacgttt caacaacgat taccgtttaa 180
agaaacggtt ataactagcc ttcaagtagg ccacactagt gtaacgctct tcagcgggca 240
ct 242

<210> SEQ ID NO 11
<211> LENGTH: 242
<212> TYPE: RNA
<213> ORGANISM: Cowpea chlorotic mottle virus

<400> SEQUENCE: 11
ggucuccuua gagaucaccu agucuuucga cuaggcgcug cccaccaguc uuauuaccuc 60
acuaugugag guacugguac gaacuccaaa gaguucuucc gaaggguuca aggaguaaaa 120
cccaagggca gcucaauccu cuuguaaaag gaagacguuu caacaacgau uaccguuuaa 180
agaaacgguu auaacuagcc uucaaguagg ccacacuagu guaacgcucu ucagcgggca 240
cu 242

<210> SEQ ID NO 12
<211> LENGTH: 12
<212> TYPE: DNA
<213> ORGANISM: Artificial
<220> FEATURE:
<223> OTHER INFORMATION: Artificial sequence used to show antisense
relationship of a gene and IRES to a promoter and viral 3' UTR
<220> FEATURE:
<221> NAME/KEY: misc_feature
<222> LOCATION: (1)..(3)
<223> OTHER INFORMATION: n is a, c, g, or t

<400> SEQUENCE: 12
nnncatggaa tt 12

<210> SEQ ID NO 13
<211> LENGTH: 12
<212> TYPE: DNA
<213> ORGANISM: Artificial
<220> FEATURE:
<223> OTHER INFORMATION: Complement of artificial sequence used to show
antisense relationship of a gene and IRES to a promoter and viral
3' UTR
<220> FEATURE:
<221> NAME/KEY: misc_feature -continued

```
<222> LOCATION: (10)..(12)
<223> OTHER INFORMATION: n is a, c, g, or t

<400> SEQUENCE: 13

aattccatgn nn                                                          12


<210> SEQ ID NO 14
<211> LENGTH: 12
<212> TYPE: RNA
<213> ORGANISM: Artificial
<220> FEATURE:
<223> OTHER INFORMATION: Transcript of RNA polymerase
<220> FEATURE:
<221> NAME/KEY: misc_feature
<222> LOCATION: (1)..(3)
<223> OTHER INFORMATION: n is a, c, g, or u

<400> SEQUENCE: 14

nnncauggaa uu                                                          12


<210> SEQ ID NO 15
<211> LENGTH: 12
<212> TYPE: RNA
<213> ORGANISM: Artificial
<220> FEATURE:
<223> OTHER INFORMATION: Complement of transcript of RNA polymerase
<220> FEATURE:
<221> NAME/KEY: misc_feature
<222> LOCATION: (10)..(12)
<223> OTHER INFORMATION: n is a, c, g, or u

<400> SEQUENCE: 15

aauuccaugn nn                                                          12


<210> SEQ ID NO 16
<211> LENGTH: 12
<212> TYPE: DNA
<213> ORGANISM: Artificial Sequence
<220> FEATURE:
<223> OTHER INFORMATION: DNA Construct containing promoter complementary
      coding sequence, exemplary IRES complementary sequence and a viral
      3' UTR in 5' - 3' orientation
<220> FEATURE:
<221> NAME/KEY: misc_feature
<223> OTHER INFORMATION: DNA construct wherein YYY indicates
      complementary first translatable codon after initiation codon and
      an asterisk indicates a stop codon.

<400> SEQUENCE: 16

yyycatggaa tt                                                          12


<210> SEQ ID NO 17
<211> LENGTH: 12
<212> TYPE: DNA
<213> ORGANISM: Artificial Sequence
<220> FEATURE:
<223> OTHER INFORMATION: DNA Construct containing promoter, coding
      sequence, exemplary IRES sequence and a viral 3' UTR in 3' - 5'
      orientation
<220> FEATURE:
<221> NAME/KEY: misc_feature
<223> OTHER INFORMATION: DNA construct wherein XXX indicates first
      translatable codon after initiation codon and an asterisk
      indicates a stop codon.

<400> SEQUENCE: 17

yyygtacctt aa                                                          12


<210> SEQ ID NO 18
```

-continued

```
<211> LENGTH: 12
<212> TYPE: RNA
<213> ORGANISM: Artificial Sequence
<220> FEATURE:
<223> OTHER INFORMATION: RNA Construct containing complementary coding
      sequence, exemplary IRES complementary sequence and a viral 3' UTR
      in 5' - 3' orientation
<220> FEATURE:
<221> NAME/KEY: misc_feature
<223> OTHER INFORMATION: Recombinant RNA sequence where YYY is the
      complement of the first codon after the initiation codon and where
      an asterisk indicates a stop codon.

<400> SEQUENCE: 18

yyycauggaa uu                                                          12


<210> SEQ ID NO 19
<211> LENGTH: 12
<212> TYPE: RNA
<213> ORGANISM: Artificial Sequence
<220> FEATURE:
<223> OTHER INFORMATION: RNA Construct containing viral 3' UTR,
      exemplary IRES sequence and a coding sequence in 5' - 3'
      orientation
<220> FEATURE:
<221> NAME/KEY: misc_feature
<223> OTHER INFORMATION: Complementary sequence (sense strand) of RNA
      recombinant sequence where XXX is the first translatable codon
      after initiation codon and where an asterisk indicates a stop
      codon.

<400> SEQUENCE: 19

aauuccaugy yy                                                          12
```

EXPRESSION OF A RECOMBINANT TRANSGENE

FIELD

The present invention relates generally to virology, in particular to the use of a positive strand RNA virus to express a heterologous polypeptide in a transgenic host cell.

BACKGROUND

A transgene construct for expressing a heterologous polypeptide in a host cell, seed or organism usually comprises a promoter operably linked to a nucleic acid encoding a heterologous polypeptide. However, transgene expression can be toxic to the host cell, seed or organism, or inhibit growth of the host cell, seed or organism. Furthermore, in the case of transgenic plants, transgenic crop seed can contaminate non-transgenic seed, causing the appearance of an unwanted heterologous polypeptide in a crop. One solution to such problems has been to provide transgene constructs comprising an inducible promoter. In a host cell, cell culture, or organism harboring a transgene comprising an inducible promoter controlling a transgene, expression of the transgene can be delayed until the host cell, cell culture, or organism reaches a predetermined condition or stage of development, size, or cell density. Transcription of the transgene is then induced using a stimulus appropriate for the promoter. However, a significant problem with the use of an inducible promoter to direct transgene expression is that an inducible promoter can support background levels of transgene transcription (i.e., are "leaky") in the absence of the stimulus. Thus, the host cell comprises RNA coding for the heterologous polypeptide, even in the absence of the stimulus. This RNA can be translated, resulting in background levels of heterologous polypeptide. For example, in host cells comprising a recombinant inducible promoter, the molar concentration ratio of a heterologous polypeptide in an induced host cell compared to an uninduced host cell, can be, for example, about 10:1. Expression of a transgene due to leaky transcription from an inducible promoter can lead to the same kinds of problems encountered when a constitutively active promoter is used. Therefore, it would be useful to provide a system for transgene expression in which the level of expression of the transgene in an unstimulated cell is not measurably greater than in a non-transgenic cell of the same type.

RNA viruses, nucleic acids thereof, and DNA copies of RNA viral sequences have been used to control expression of transgenes. RNA viruses can comprise single-stranded RNA or double-stranded RNA. Single-stranded RNA viruses are either "positive-strand" or "negative-strand" RNA viruses. A positive-strand single-stranded RNA virus comprises sequence in the same reading sense as viral mRNA(s). With the exception of positive strand single-stranded RNA retroviruses, which use a DNA intermediate, replication and transcription of a positive-strand RNA virus involves synthesis of a complementary (negative strand) RNA copy of the viral genome. Synthesis of a complementary RNA copy requires an RNA-dependent RNA polymerase (RDRP) encoded within the viral genome. Viral replication in a cell involves a replication complex comprising the RDRP. During the replication process, the replication complex binds to the 3' untranslated region (3' UTR) of the viral RNA, and initiates synthesis of the complementary strand (van Rossum, C. M. A., et al., *J. Gen. Virol.* 78: 3045-3049, 1997).

U.S. Pat. No. 6,433,248 B1 to Lommel et al. discloses a method of activating transcription of an RNA of interest in a cell. The disclosed method includes the steps of (a) providing a host cell containing a heterologous construct, the heterologous construct comprising an RNA virus subgenomic promoter operatively associated with a heterologous RNA of interest, wherein the promoter does not initiate transcription of the heterologous RNA in the absence of a corresponding RNA virus trans-activating RNA segment, and where the RNA virus trans-activating RNA segment is absent from the host cell; and (b) introducing a trans-activating nucleic acid segment into the host cell so that transcription of the heterologous RNA is initiated. The method relies on the use of a viral trans-activating RNA segment, and because of the presence of RNA comprising coding sequence for the heterologous polypeptide in an uninduced host, is still subject to background levels of expression. Furthermore, unlike the present disclosure, the method does not utilize an RNA sequence complementary to an internal ribosome entry site.

U.S. Pat. No. 6,462,255 B1 to Thurpen discloses high level expression of foreign genes in plants using viral replicons, wherein the replicons code for at least one foreign gene and possess sequences required in cis for replication. Unlike the present disclosure, because of the presence of RNA comprising coding sequence for the heterologous polypeptide in an uninduced host, the methods described are still subject to background levels of expression. Furthermore, the patent does not disclose an RNA comprising an antisense coding sequence, and anti-IRES, and a 3' UTR as set forth in the present disclosure.

U.S. Pat. No. 6,326,480 B1 to Kovelman et al. discloses a reporter system for assaying positive strand RNA virus replication. The invention describes antisense reporter plasmids comprising a promoter operably linked to a DNA sequence encoding: (a) a sequence complementary to the 3' end of a viral genome; (b) a reporter gene in antisense orientation; and (c) a sequence complementary to the 5' end of the viral genome. The patent further describes antisense reporter mRNAs encoding: (a) a sequence complementary to a 3' end of a viral genome; (b) a reporter gene in antisense orientation; and (c) a sequence complementary to a 5' end of the viral genome. Unlike the present disclosure, this patent does not disclose a recombinant RNA comprising a sequence complementary to the coding sequence of a heterologous polypeptide, a sequence complementary to an internal ribosome entry site, and a viral 3' untranslated region, nor does it describe a recombinant mRNA molecule comprising an internal ribosome binding site operably linked to an RNA sequence encoding a heterologous polypeptide and the complement of an internal ribosome entry site.

US Patent Application Publication US 2002/0138873 A1 to Lewandowski et al. discloses a multiple component RNA vector system, consisting of an RNA replicon comprising a 5' non-translated region, an open reading frame (ORF) homologous to an ORF of an intact or fragments of a non-structural protein of an RNA virus, a sequence non-native to the RNA virus, and a 3' non-translated region. The recombinant RNA molecules of the present invention do not require an open reading frame (ORF) homologous to an ORF of an intact or fragments of a non-structural protein of an RNA virus or a 5' non-translated region.

Powell et al. (*Proc. Natl. Acad. Sci. USA* 86: 6949-6952, 1989) disclosed transgenic tobacco plants that express RNA sequences complementary to the tobacco mosaic virus coat protein coding sequence comprising a tRNA-like structure at the 3' end of the TMV RNA. Transgenic plants that expressed RNA sequences complementary to the coat protein coding region and the 3' untranslated region, including the tRNA-like sequences, when challenged with TMV, were protected from infection at low levels of inoculum. These findings did not disclose synthesis or expression of an RNA comprising the complement of a 3' UTR, an IRES and coding sequence of a heterologous polypeptide.

Zaccomer et al (Gene 136: 87-94, 1993) reported experiments with transgenic rapeseed (*Brassica napus*) in which the transgenes comprised either a sense or antisense coding sequence of a chloramphenicol acetyltransferase (CAT) gene upstream from a positive strand 3'-terminal 100 nucleotides of the noncoding region of the turnip yellow mosaic virus. RNA complementary to the initial transcript was detected after infection of a host transgenic plant with turnip yellow mosaic virus.

These findings did not disclose synthesis or expression of an RNA comprising the complement of a 3' UTR, an IRES and coding sequence of a heterologous polypeptide.

Teycheney et al (*J. Gen. Virol.* 81: 1121-1126, 2000) reported that transcripts of transgenes comprising the 3' UTR of Lettuce mosaic virus could serve as template for synthesis of complementary negative strand RNA following infection of host tobacco plants with Tobacco etch virus, Tobacco vein mottle virus or Pepper mottle virus, but not with Cucumber mosaic virus. These workers also showed that deletion of the 3' UTR from the transgene abolished the synthesis of negative strands. These findings did not disclose synthesis or expression of an RNA comprising the complement of a 3' UTR, an IRES and coding sequence of a heterologous polypeptide.

Therefore, provision of a recombinant RNA comprising a sequence complementary to the coding sequence of a heterologous polypeptide (an “anti-sense coding sequence”), a sequence complementary to an internal ribosome entry site (an “anti-IRES”), and a viral 3' untranslated region (3' UTR) as set forth herein, and which is not expected to provide sense strand coding sequence for a heterologous polypeptide prior to stimulation or activation of synthesis of a complementary strand of the recombinant RNA, has not been reported or suggested heretofore.

SUMMARY

Accordingly, the inventors herein have succeeded in developing a transgene expression system. The system includes the provision of a recombinant RNA comprising a complementary copy of coding sequence of a heterologous polypeptide, a complementary copy of an internal ribosome entry site (IRES) (Strauss and Strauss, Viruses and Human Disease, Academic Press, 24-25, 2002) and a 3' untranslated region of a positive strand single-stranded RNA virus. Because coding sequence is expected to be absent in the host cell or organism prior to introduction or application of a stimulus that introduces an RNA-directed RNA polymerase (RDRP) for formation of a complementary copy of the RNA in the host cell or organism, the amount of the complementary copy of the recombinant RNA and the heterologous polypeptide are expected to be no greater than that of a non-transgenic control cell or organism. Therefore, the expression levels of the RNA complement of the recombinant RNA or heterologous polypeptide in the absence of the stimulus or activating signal are expected to be below detection limits, even when highly sensitive detection means such as reverse transcription-polymerase chain reaction (for the RNA) or radioimmunoassay (for the polypeptide) are used. The amount of the RNA complement of the recombinant RNA comprised by a cell not provided a stimulus is expected to be, for example, less than about 1000 copies per cell, less than about 100 copies per cell, less than about 10 copies per cell, or zero copies per cell. Furthermore, the amount of the heterologous polypeptide comprised by a cell not provided a stimulus is expected to be, for example, less than about 1000 copies per cell, less than about 100 copies per cell, less than about 10 copies per cell, or zero copies per cell. The molar concentration ratio of RNA complementary to the recombinant RNA in a cell provided a stimulus relative to a cell not provided a stimulus is expected to be, for example, at least about 50:1, at least about 100:1, at least about 1000:1, or at least about 10,000:1. The molar concentration ratio of heterologous polypeptide in a cell provided a stimulus relative to a cell not provided a stimulus is expected to be, for example, at least about 50:1, at least about 100:1, at least about 1000:1, or at least about 10,000:1.

The system can be used to express heterologous polypeptides in a host cell exposed to an activator or stimulus for synthesis of the RNA complement of the recombinant RNA. The activator or stimulus can be any extrinsic signal that results in the assembly of a replication complex in the host cell, wherein the replication complex comprises an RNA-dependent RNA polymerase. The activator or stimulus provides at least one required component of the replication complex, such as, for example, an RNA-dependent RNA polymerase. The at least one component of the replication complex can be, for example, an RNA-dependent RNA polymerase encoded by a positive strand single-stranded RNA virus. The replication complex recognizes and binds to the viral 3' UTR of the recombinant RNA, and initiates synthesis of the complementary copy of the recombinant RNA. Because the complementary copy of the recombinant RNA comprises an IRES operably linked to a sequence encoding a heterologous polypeptide, host cell ribosomes bind to and translate the sequence encoding the heterologous polypeptide.

The system can therefore be used to restrict expression to cells subjected to the activator or stimulus. The activator or stimulus can be, for example, a positive strand single-stranded RNA virus; an incomplete positive strand single-stranded RNA virus comprising the viral genes required for establishment of a replication complex, such as, for example, an RNA-dependent RNA polymerase; a virus incapable of plant-to-plant spread, or a nucleic acid thereof. The nucleic acid can be one or more RNA species comprised by a positive strand single-stranded RNA virus, or can be one or more cDNAs thereof. A vector can comprise a promoter operably linked to the cDNA.

The system can be used, for example, to express a phytotoxic polypeptide in a host cell of a plant, such as, for example, a food crop plant. Upon infection of the host cell with a positive strand single-stranded RNA virus, such as, for example, a pathogenic plant RNA virus introduced to a plant cell by an insect or nematode vector, the phytotoxic polypeptide is expected to disable or destroy the cell, thereby protecting the plant from viral replication and spread of a disease mediated by the RNA virus. Because expression is restricted to a host cell or cells activated by a stimulus, such as, for example, a virus infection, a viral RNA transfection or a viral cDNA transfection, the amount of the phytotoxic polypeptide can be extremely low as a percentage of total polypeptide of the host plant. Therefore, the presence of the transgene in a food crop plant or plant cell can be acceptable in terms of environmental impact, safety, or regulations concerning genetically modified foods. The system can also be used, for example, in a plant to produce a useful polypeptide, such as, for example, an economically useful polypeptide such as, for example, a pharmaceutically useful polypeptide. Because the background levels of expression in a transgenic cell or plant of either the RNA coding the polypeptide, or the polypeptide itself, are expected to be no greater than that of non-transgenic control cell or plant, and can be zero or below detection limits, it is expected that the invention will allow a plant comprising a transgene of the invention to be planted, grown or harvested with low risk of uncontrolled introduction of a heterologous polypeptide into the environment. Similarly, system can also be used, for example, in a plant to produce a polypeptide conferring disease resistance to the plant, such as, for example, a viral polypeptide such as, for example, a viral coat protein polypeptide (Fitchen and Beachy, *Annual Rev. Microbiol.* 47: 739-763, 1993; Powell-Abel et al., 1986; Powell et al., *Proc. Natl. Acad. Sci. USA* 86: 6949-6952, 1989; Zaccomer et al., *Gene* 136: 87-94, 1993).

The present invention is, therefore, directed in general to a recombinant RNA molecule comprising, in 5' to 3' direction, an anti-sense coding sequence of a heterologous polypeptide (including an antisense translation initiation codon), a complement of an internal ribosome entry site (IRES), and a 3' untranslated region (3' UTR) of a positive strand single-stranded RNA virus, (FIG. 1B). Preferably, the positive strand single-stranded RNA virus is a positive strand single-stranded RNA virus having no DNA stage. A host cell can comprise the recombinant RNA sequence. The host cell is expected to synthesize neither an RNA encoding the heterologous polypeptide, nor the heterologous polypeptide itself in the absence of an activator or stimulus for synthesis of the complementary strand of the recombinant RNA. Preferably, the activator is a helper RNA virus or a portion thereof that encodes an RNA-directed RNA polymerase, or the nucleic acid thereof. Preferably, the helper virus is a positive strand single-stranded RNA virus. Preferably, the positive strand single-stranded RNA virus is a positive strand single-stranded RNA virus having no DNA stage. Preferably, the helper virus is a plant virus, such as, for example, a plant virus incapable of plant-to-plant spread. Preferably, the helper virus is a complete virus. Upon infection or transfection of a transgenic host cell expressing the recombinant RNA with a positive strand single-stranded RNA virus or the nucleic acid thereof, a viral RNA-dependent RNA polymerase is expressed, and a replication complex forms which comprises the RDRP. The replication complex binds to and initiates synthesis from the 3' UTR of the recombinant RNA. The trans-acting activator thereby stimulates synthesis of the RNA complement of the recombinant RNA in the infected cell. The RNA complement of the recombinant RNA comprises, in 5' to 3' direction, the complement of the 3' UTR, an IRES, and coding sequence for the heterologous polypeptide, wherein the IRES is operably linked to the coding sequence for the heterologous polypeptide (FIG. 1C). The provision of an IRES operatively linked to coding sequence of a heterologous polypeptide thereby provides an RNA molecule that a ribosome can bind (at the IRES) and translate (starting at an initiation codon of the coding sequence) (FIG. 1*b*, FIG. 5*b*, FIG. 6*b*). Therefore, the RNA complementary to the recombinant RNA (FIG. 1*c*, FIG. 5*c*, FIG. 6*c*) is expected to bind to a ribosome at the IRES, and the coding sequence is expected to be read by the ribosome for synthesis of the heterologous polypeptide. An uninduced cell comprising the transgene does not synthesize a sense copy of the RNA sequence encoding a heterologous polypeptide, so that heterologous polypeptide synthesis is expected to be no greater than that of a control, non-transgenic cell. Therefore, the level of expression of the heterologous polypeptide in an uninduced transgenic cell or organism is expected to be, for example, less than about 1000 copies per cell, less than about 100 copies per cell, less than about 10 copies per cell, or zero copies per cell.

Thus, in one embodiment, the invention is directed to a recombinant DNA transgene encoding a recombinant RNA molecule. In preferred embodiments, the DNA transgene comprises a promoter recognized by a DNA-dependent RNA polymerase comprised by the host cell, wherein the promoter is operably linked, in the 5' to 3' direction, to a DNA sequence comprising an anti-sense coding sequence for a heterologous polypeptide, a sequence complementary to an IRES, and a 3' UTR of a positive strand single-stranded RNA virus. The 3' UTR of a positive strand single-stranded RNA virus can be a 3' UTR of a positive strand single-stranded RNA virus having no DNA stage. Preferably, the 3' UTR of a positive strand single-stranded RNA virus having no DNA stage is a 3' UTR of a positive strand single-stranded RNA plant virus having no DNA stage (FIG. 1*a*, FIG. 5*a*, FIG. 6*a*).

One embodiment of the method is the provision of a method of conferring disease resistance to a transgenic plant. The method comprises providing a transgenic plant comprising a recombinant DNA molecule comprising a promoter operably linked to a DNA sequence comprising, in the 5' to 3' direction, a sequence complementary to a coding sequence for a heterologous polypeptide capable of conferring disease resistance, a sequence complementary to an internal ribosome entry site, a 3' UTR of a first positive strand single-stranded RNA virus; and growing the transgenic plant, whereby resistance is conferred to infection from a second positive strand single-stranded RNA virus.

The promoter can be a constitutive promoter or an inducible promoter. Preferably, the promoter is a constitutive promoter. Preferably, the promoter is a Cauliflower mosaic virus 35S promoter. In some embodiments, the DNA transgene can further comprise a cis-acting transcription terminator situated 3' to the 3' UTR.

In another aspect, the invention is directed to a host cell comprising the recombinant DNA transgene. A host cell chromosome, or an extrachromosomal a vector, such as a plasmid or virus, can comprise the DNA transgene. In preferred embodiments, the host cell is a plant cell.

In another aspect, the invention is directed to a host organism comprising the host cell comprising the recombinant DNA transgene. Preferably, the host organism is a plant, more preferably a *Nicotiana* plant, more preferably a *Nicotiana benthamiana* plant.

In another embodiment, the invention is directed to a recombinant RNA molecule, wherein the recombinant RNA molecule comprises, in 5' to 3' direction, an anti-sense coding sequence for a heterologous polypeptide, an anti-sense IRES, and a 3' UTR of a positive strand single-stranded RNA virus.

In another aspect, the invention is directed to a host cell comprising the recombinant RNA molecule. In preferred embodiments, the host cell is a plant cell.

In another aspect, the invention is directed to a host organism comprising the host cell comprising the recombinant RNA molecule. Preferably, the host organism is a plant, more preferably a *Nicotiana* plant, more preferably a *Nicotiana benthamiana* plant.

In one embodiment, the invention is directed to the complement of a recombinant RNA molecule, wherein the RNA complement of the recombinant RNA molecule comprises, in 5' to 3' direction, the complement of a 3' UTR of a positive strand single-stranded RNA virus, an IRES, and coding sequence for a heterologous polypeptide.

In another aspect, the invention is directed to a host cell comprising the RNA complement of the recombinant RNA molecule. In preferred embodiments, the host cell is a plant cell. Because the RNA complement of the recombinant RNA molecule comprises an IRES operably linked to a sequence encoding a heterologous polypeptide, the host cell is expected to express the heterologous polypeptide.

In another aspect, the invention is directed to a host organism comprising the host cell comprising the RNA complement of the recombinant RNA molecule. Preferably, the host organism is a plant, more preferably a *Nicotiana* plant, more preferably a *Nicotiana benthamiana* plant.

In another embodiment, the invention is directed to a host cell comprising a heterologous polypeptide encoded by coding sequence comprised by the complement of a recombinant RNA, wherein the RNA complement of the recombinant RNA comprises, in 5' to 3' direction, the complement of a 3' UTR of a positive strand single-stranded RNA virus, an IRES, and coding sequence for a heterologous polypeptide.

In certain aspects, the RNA virus source of the 3' UTR of the recombinant RNA molecules described herein, is preferably a positive strand single-stranded RNA virus. Preferably, the positive strand single-stranded RNA virus is a positive strand single-stranded RNA virus having no DNA stage. A positive strand single-stranded RNA virus having no DNA stage providing a source of a 3' UTR can be a positive strand single-stranded RNA virus that infects animal cells or human cells (an "animal virus") or a positive-strand single-stranded RNA virus having no DNA stage that infects plants (a "plant virus"). Preferably, the virus is a positive strand single-stranded RNA plant virus having no DNA stage.

In certain aspects, the RNA virus that can be used to stimulate synthesis of the RNA complement of the recombinant RNA upon infection or transfection of viral nucleic acid is preferably a positive strand single-stranded RNA viruses. A positive strand single-stranded RNA virus can be a positive strand single-stranded RNA virus that infects animal cells or human cells (an "animal virus") or a positive-strand single-stranded RNA virus that infects plants (a "plant virus"). Preferably, the virus is a positive strand single-stranded RNA virus having no DNA stage. Preferably, the virus is a positive strand single-stranded RNA plant virus. Preferably, the virus produces an RNA-dependent RNA polymerase which can comprise a replication complex that can bind to the 3' UTR of the recombinant RNA and catalyze synthesis of the complement of a recombinant RNA comprising the 3' UTR. The virus used to stimulate synthesis of the RNA complement of the recombinant RNA upon infection or transfection of viral nucleic acid can be identical to the virus used as the source of the 3' UTR of the transgene. The virus used to stimulate synthesis of the RNA complement of the recombinant RNA can also be different from the virus source of the 3' UTR, provided that the replication complex formed upon infection or transfection of the stimulating viral nucleic acid recognizes the 3' UTR of the recombinant RNA. Recognition of the 3' UTR of the recombinant RNA by an infecting or transfecting virus can be determined by standard methods known in the art (for example, the methods disclosed in Teycheney et al., *J. Gen. Virol.* 81: 1121-1126, 2000).

In another embodiment, the invention is directed to a method of synthesizing a heterologous polypeptide. The method comprises providing a transgenic host cell comprising a recombinant DNA transgene in which the cell transcribes the recombinant DNA transgene and thereby accumulates a recombinant RNA molecule, and stimulating or activating the synthesis of an RNA complementary to the recombinant RNA molecule. In this method, the recombinant DNA transgene can comprise a promoter operably linked, in 5' to 3' order, to a DNA sequence comprising a sequence complementary to the coding sequence for a heterologous polypeptide, a DNA sequence complementary to an IRES, and a DNA sequence corresponding to a 3' UTR of a positive strand single-stranded RNA virus. As shown in FIG. 6, the DNA transgene includes a template strand reading from the 3' to the 5' direction of a DNA sequence comprising a promoter, a coding sequence for a heterologous polypeptide, a coding sequence to an IRES, and a DNA sequence corresponding to a complementary sequence to the coding sequence of a 3' UTR of a positive strand single-stranded RNA virus. The transgene can also include sequence complementary to one or more intervening sequences ("introns"), and, at the 3' end, a transcription terminator. A recombinant RNA transcribed from DNA of the transgenic host cell can comprise, in 5' to 3' order, an RNA sequence complementary to the coding sequence for a heterologous polypeptide, an RNA sequence complementary to an IRES, and a 3' UTR of a positive strand single-stranded RNA virus. Stimulating or activating synthesis of an RNA complementary to the recombinant RNA can result in synthesis of an RNA sequence comprising the complement of a 3' UTR of a positive strand single-stranded RNA virus, an IRES, and coding sequence of a heterologous polypeptide, wherein the IRES and the coding sequence are operably linked. Host cell ribosomes are expected to bind to the RNA complementary to the recombinant RNA and translate the coding sequence, thereby forming the heterologous polypeptide. Stimulating the synthesis of the RNA complement of the recombinant RNA molecule can comprise infecting the host cell with a positive strand single-stranded RNA virus, transfecting the host cell with a cDNA of a positive strand single-stranded RNA virus or transfecting the host cell with RNA of a positive strand single-stranded RNA virus. The transfecting can be by any transfection method known in the art. It is believed that RNA of a positive strand single-stranded RNA virus, upon infection or transfection of the host cell, is translated by host cell ribosomes, thereby providing polypeptide components comprised by a replication complex, such as, for example, an RNA-dependent RNA polymerase. A replication complex is expected to bind to the 3' UTR of the recombinant RNA, and initiate synthesis of an RNA complementary to the recombinant RNA starting at the 3' UTR. Elongation synthesis of RNA complementary to the recombinant RNA is expected to follow initial binding of the replication complex to the 3' UTR. Translation of the coding sequence comprised by the RNA complementary to the recombinant RNA comprises ribosomes recognizing and binding the IRES, and initiating translation of the coding sequence operably linked to the IRES. Translation of the coding sequence yields the heterologous polypeptide.

In another aspect, the invention is directed to transgenic seed comprising a recombinant DNA transgene encoding a recombinant RNA molecule. In preferred embodiments, the DNA transgene comprises a promoter recognized by a DNA-dependent RNA polymerase, wherein the promoter is operably linked, in 5' to 3' direction, to a sequence comprising an anti-sense coding sequence for a heterologous polypeptide, a sequence complementary to an IRES, and a 3' UTR of a positive strand single-stranded RNA virus. In some embodiments, the DNA transgene further comprises a cis-acting transcription terminator situated 3' to the 3' UTR. Preferably, the transgene can be integrated into the seed genome and can be present in cells of plants grown from the seed.

In another embodiment, the invention is directed to a method of making a transgenic cell comprising a recombinant DNA transgene encoding a recombinant RNA molecule. In preferred embodiments, the DNA transgene comprises a promoter recognized by a DNA-dependent RNA polymerase, wherein the promoter is operably linked, in 5' to 3' direction, to a DNA sequence comprising an anti-sense coding sequence for a heterologous polypeptide, a sequence complementary to an IRES, and a 3' UTR of a positive strand single-stranded RNA virus. The method comprises introducing the transgene to a cell. The introducing the transgene can comprise using any method known in the art to introduce heterologous DNA to a cell. For example, the introducing the recombinant DNA can comprise bombarding a cell with the DNA using a "gene gun," contacting the cell with a virus vector comprising the recombinant DNA, or contacting the cell with bacteria such as a transgenic *Agrobacterium tumefaciens* comprising a recombinant Ti plasmid comprising a transgene.

In another embodiment, the invention is directed to a DNA molecule for construction of a vector for expressing a heterologous polypeptide in a transgenic cell, the DNA molecule comprising a promoter operably linked, in the 5' to 3' direction, to at least one site for insertion of a sequence comprising coding sequence of a heterologous polypeptide in an antisense orientation, an anti-IRES, and a 3' UTR of a positive strand single-stranded RNA virus. The at least one site for insertion of a sequence comprising coding sequence of a heterologous polypeptide in an antisense orientation can comprise at least one recombination site and/or at least one restriction site. The at least one recombination site can be, for example, a bacteriophage lambda an site or a topoisomerase I-based recombination site, and the at least one restriction site can be, for example, a polylinker. The DNA molecule of this embodiment facilitates the construction of a DNA comprising, in the 5' to 3' direction, a promoter, an anti-sense coding sequence of a heterologous polypeptide in an antisense orientation, an anti-IRES, and a 3' UTR of a positive strand single-stranded RNA virus. This DNA molecule can itself be a vector, such as, for example, a virus or a plasmid. The DNA molecule can further comprise sequences additional sequences, such as, in non-limiting example, a sequence complementary to a sequence encoding a leader peptide or a transcription termination site.

In a related aspect, the invention is directed to a method of making a transgenic vector for expression of a heterologous polypeptide in a transgenic cell. The method comprises providing a DNA molecule comprising a promoter operably linked, in the 5' to 3' direction, to at least one site for insertion of a sequence comprising coding sequence of a heterologous polypeptide in an antisense orientation, a sequence complementary to an internal ribosome entry site, and a 3' UTR of a positive strand single-stranded RNA virus, and inserting a sequence encoding a heterologous polypeptide into the insertion site of the DNA molecule in an antisense orientation relative to the direction of transcription from the promoter. The inserting can be by any means known in the art. A recombinant DNA molecule comprising a promoter operably linked to a DNA sequence comprising, in the 5' to 3' direction, a sequence complementary to a coding sequence for a heterologous polypeptide, a sequence complementary to an internal ribosome entry site and a 3' UTR of a positive strand single-stranded RNA virus.

In a related embodiment, the invention is directed to a kit for constructing a vector for expressing a heterologous polypeptide in a transgenic cell. The kit can comprise a DNA molecule comprising a promoter operably linked, in the 5' to 3' direction, to at least one site for incorporation of coding sequence of a heterologous polypeptide in an antisense orientation, an anti-IRES, and a 3' UTR of a positive strand single-stranded RNA virus, and packaging. A user of the kit can, for example, incorporate coding sequence for a heterologous polypeptide into the DNA vector such that transcription of the vector would yield a transcript comprising, in the 5' to 3' direction, the complement of the coding sequence, the complement of the IRES, and the 3' UTR. In some aspects, the kit can further comprise a positive strand single-stranded RNA virus or nucleic acid thereof that, upon infection or transfection, would support the formation of an RNA complementary to the recombinant RNA. In some aspects, the kit can further comprise a host organism for growing the vector, such as, for example, transformation-competent *E. coli*. In some aspects, the kit can further comprise instructions.

In a related aspect, the invention is directed to a method of forming a host cell comprising a transgene comprising a promoter operatively linked to a DNA sequence comprising, in 5' to 3' order, a sequence complementary to a sequence encoding a heterologous polypeptide, a sequence complementary to an IRES, and a sequence comprising a 3' UTR of an RNA virus. The method comprises transforming or infecting the host cell with the DNA. The transforming or infecting can be by any method known in the art.

BRIEF DESCRIPTION OF THE DRAWINGS

FIG. 1 illustrates the organization of nucleic acids described herein. (a) A DNA transgene, wherein "Promoter" represents a promoter for transcription of the transgene; "a-coding" represents DNA sequence complementary to coding sequence of a heterologous polypeptide; "a-IRES" represents DNA sequence complementary to DNA sequence encoding an IRES; and "3' UTR" represents DNA sequence corresponding to a 3' untranslated region of a positive strand single-stranded RNA virus. Polarity of the DNA is indicated by "5'" and "3'" at the ends, and by an arrow at the 3' end. (b) A recombinant RNA, wherein "α-coding" represents antisense coding sequence of a heterologous polypeptide; "α-IRES" represents RNA sequence complementary to an IRES; and "3' UTR" represents RNA sequence of a 3' untranslated region of a positive strand single-stranded RNA virus. Polarity of the RNA is indicated by "5'" and "3'" at the ends, and by an arrow at the 3' end. (c) An RNA complementary to the recombinant RNA of (b), wherein "α-3' UTR" represents RNA sequence complementary to a 3' UTR of a positive strand single-stranded RNA virus; "IRES" represents an internal ribosome entry site, and "coding" represents RNA sequence encoding a heterologous polypeptide.

FIG. 5 illustrates generalized arrangement of components in planta. (a) Double strand DNA transgene complex. The plant RNA polymerase II recognizes the transcriptional promoter and produces the RNA transcript shown in (b). (b) An RNA polymerase II (Pol II) transcript of the DNA transgene shown in (a). The Pol II transcript is transported to the cytoplasm where it awaits the virus that recognizes its 3' UTR as a replication initiation site. Upon introduction of the appropriate RNA virus, the viral replication complex recognizes its 3' UTR and makes a complementary RNA copy (c) of the Pol II transcript. (c) A complementary RNA copy of the Pol II transcript shown in (b). The functional IRES enables the entry of a ribosome and the translation of the transgene that is now in the sense orientation.

FIG. 6 illustrates a detailed arrangement of components in planta. (a) illustrates the antisense relationship of the gene and IRES (SEQ ID NOs: 16 & 17) with respect to the promoter and the viral 3' UTR. Upside down nucleotides indicate antisense orientation. (b) illustrates the RNA polymerase transcript with the gene and IRES (SEQ ID NO: 18) in upside down antisense orientation. (c) illustrates final conversion resulting in both the IRES and gene (SEQ ID NO: 19) in a translatable orientation. AATTCC indicates IRES; ATG indicates initiation codon; XXX indicates any codon; YYY indicates complements of a codon; asterisk indicates a stop codon.

DETAILED DESCRIPTION

Figure 2:
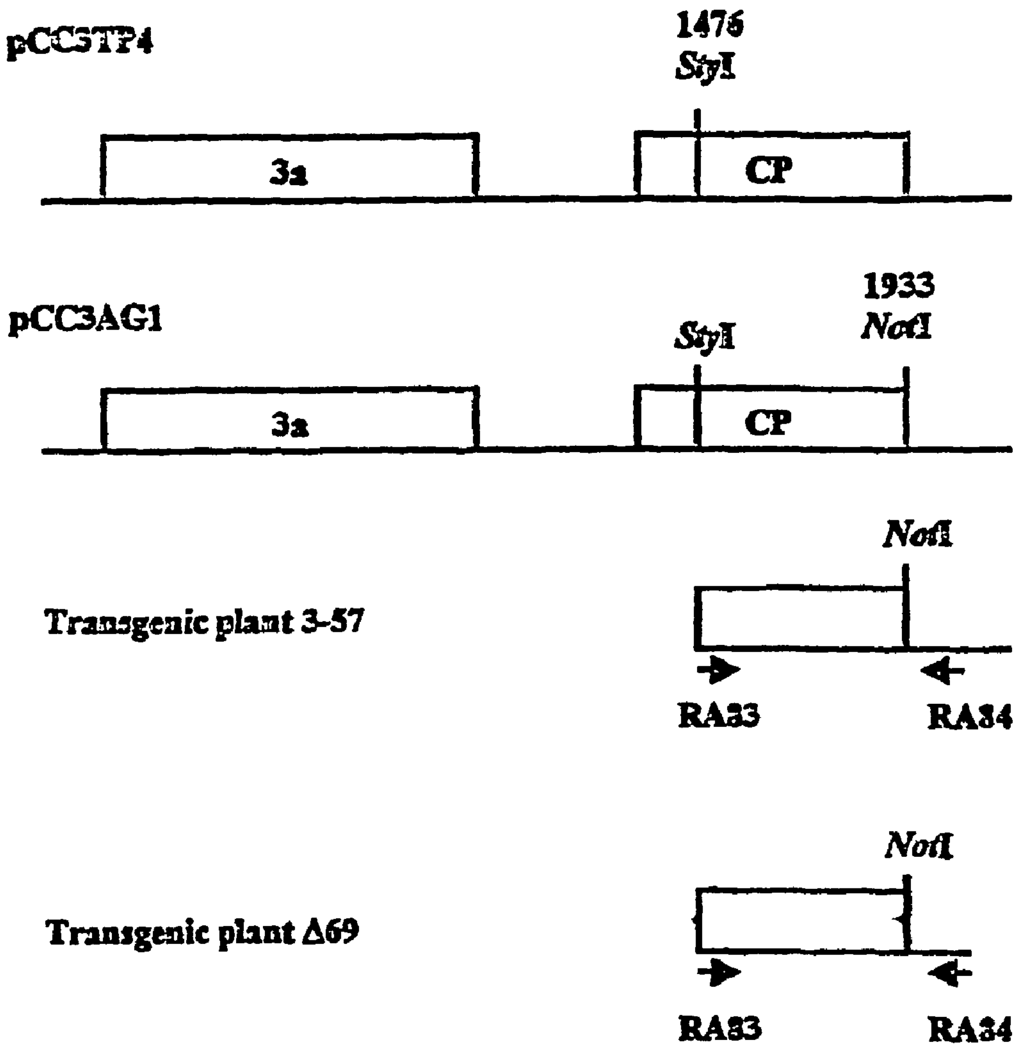
FIG. 2 illustrates plasmids used to demonstrate synthesis of RNA complementary to a recombinant RNA upon host cell infection with a positive strand single-stranded RNA virus. Wild type Cowpea chlorotic mosaic virus RNA3 has a 3a gene open reading frame (ORF) and a coat protein ORF, and is maintained in plasmid pCC3TP4. A Not I restriction site was introduced near the 3' end of the coat protein gene ORF in plasmid pCC3AG1 as well as the viral transgenes in transgenic plants 3-57 and Δ69 (Greene and Allison, *Science* 263: 1423-1425, 1994; Greene and Allison, *Virology* 225: 231-234, 1996). Transgenic plant 3-57 was transformed with the 3' 2/3 of the coat protein ORF and the full-length 3' UTR. Transgenic plant Δ69 was transformed with the same viral gene, but the 3' UTR bears a 69-nucleotide deletion at the 3' end. The negative sense RNA-specific primer RA83 (5'-AAGTGGATCCCCTC TTGTGCGGCTGC-3' (SEQ ID NO: 1)) anneals at nucleotides 1519-1544, and was used for first strand cDNA synthesis and for PCR. An additional primer RA84 (5'-ACTCCAAAGAGTTCTTCCG-3' (SEQ ID NO: 2)) anneals at nucleotides 2072-2090, and was used for PCR.

Molecular biology handbooks, such as Sambrook, J., et al., Molecular Cloning: A Laboratory Manual; Cold Spring Harbor Laboratory: Plainview, N.Y. (1990) provide guidance for standard molecular biology methods used herein. Where examples are recited herein, such examples are intended to be non-limiting.

In one embodiment, the invention is directed to a recombinant DNA transgene encoding a recombinant RNA molecule. In preferred embodiments, the DNA transgene comprises a promoter recognized by a DNA-dependent RNA polymerase, wherein the promoter is operably linked, in 5' to 3' direction, to a DNA sequence comprising an anti-sense coding sequence for a heterologous polypeptide, a sequence complementary to an IRES, and a 3' UTR of a positive strand single-stranded RNA virus.

The recombinant DNA transgene comprising the recombinant mRNA can further comprise a vector. The vector can be a plasmid, phagemid, or virus. The plasmid can be any plasmid suitable for use as a vector, in non-limiting example, a pBR322, a pBluescript® plasmid (Stratagene, La Jolla, Calif.), or a pUC plasmid. The virus is any virus suitable for use as a vector, such as, for example, a bacteriophage, such as, for example, a lambda bacteriophage. The vector can comprise sequences, such as, in non-limiting example, a prokaryotic origin of replication, a eukaryotic origin of replication, one or more selectable markers, such as, for example, a gene encoding a polypeptide that provides antibiotic resistance, such as, for example, a beta-lactamase, a polylinker, and one or more prokaryotic promoters such as, for example, a bacteriophage T3 promoter, a bacteriophage T7 promoter, or a bacteriophage Sp6 promoter. A host organism for the bacteriophage or plasmid can be any suitable prokaryotic host organism, such as, for example, an *E. coli*. The virus can also be a DNA virus or an RNA virus that can be comprised by a eukaryotic cell, such as an animal cell, a plant cell, or a cell of a microorganism such as, for example, yeast.

The promoter can be a eukaryotic promoter, and can be a eukaryotic constitutive promoter or a eukaryotic inducible promoter. The promoter can be, for example, a promoter known in the art (e.g., Praz et al., Nucleic Acids Research, 30: 322-324, 2002). The promoter can be, for example, a promoter of a naturally-occurring gene, a synthetic promoter, or a promoter of a naturally occurring gene which has been modified to alter transcription levels and/or tissue specificity. Preferably, the promoter is a eukaryotic constitutive promoter, such as, for example, a cauliflower mosaic virus (CaMV) $^{35}$S promoter, a blueberry red ringspot virus promoter, a ubiquitin gene promoter such as, for example, a maize ubiquitin 1 promoter (Cornejo et al., *Plant Mol. Biol.* 23: 567-581, 1993), an actin gene promoter such as, for example, a β-actin promoter or a rice actin-1 gene promoter (McElroy et al., *Plant Cell* 2: 163-71, 1990), an NeIF4A10 promoter (Mandel et al., *Plant Mol. Biol.* 29: 995-1004, 1995), a maize Adh1-based pEmu promoter, (Wilmink et al., *Plant Mol. Biol.* 28: 949-955, 1995), a barley leaf thionin BTH6 promoter (Holtorf et al., *Plant Mol. Biol.* 29: 637-646, 1995), a cassava vein mosaic virus (CVMV) promoter (Verdaguer et al., *Plant Mol. Biol.* 31: 1129-1139, 1996), a sugarcane bacilliform badnavirus promoter (Schenk et al., *Plant Mol. Biol.* 39: 1221-1230, 1999) or a histone gene promoter (Lepetit et al., *Mol. Gen. Genet.* 231: 276-285, 1992). Preferably, the promoter is a CAMV 35S promoter. The CaMV 35S promoter can comprises, for example, the sequence:

```
                                        (SEQ ID NO: 3)
AGATTAGCCTTTTCAATTTCAGAAAGAATGCTAACCCACAGATGGTTAGA

GAGGCTTACGCAGCAGGTCTCATCAAGACGATCTACCCGAGCAATAATCT

CCAGGAAATCAAATACCTTCCCAAGAAGGTTAAAGATGCAGTCAAAAGAT

TCAGGACTAACTGCATCAAGAACACAGAGAAAGATATATTTCTCAAGATC

AGAAGTACTATTCCAGTATGGACGATTCAAGGCTTGCTTCACAAACCAAG
```

-continued

```
GCAAGTAATAGAGATTGGAGTCTCTAAAAAGGTAGTTCCCACTGAATCAA

AGGCCATGGAGTCAAAGATTCAAATAGAGGACCTAACAGAACTCGCCGTA

AAGACTGGCGAACAGTTCATACAGAGTCTCTTACGACTCAATGACAAGAA

GAAAATCTTCGTCAACATGGTGGAGCACGACACACTTGTCTACTCCAAAA

ATATCAAAGATACAGTCTCAGAAGACCAAAGGGCAATTGAGACTTTTCAA

CAAAGGGTAATATCCGGAAACCTCCTCGGATTCCATTGCCCAGCTATCTG

TCACTTTATTGTGAAGATAGTGGAAAAGGAAGGTGGCTCCTACAAATGCC

ATCATTGCGATAAAGGAAAGGCCATCGTTGAAGATGCCTCTGCCGACAGT

GGTCCCAAAGATGGACCCCCACCCACGAGGAGCATCGTGGAAAAAGAAGA

CGTTCCAACCACGTCTTCAAAGCAAGTGGATTGATGTGATATCTCCACTG

ACGTAAGGGATGACGCACAATCCCACTATCCTTCGCAAGACCCTTCCTCT

ATATAAGGAAGTTCATTTCATTTGGAGAGAACACG
```

In the DNA sequence comprising an anti-sense coding sequence for a heterologous polypeptide, non-limiting examples of the heterologous polypeptide encoded by the complement of the anti-sense coding sequence, include, for illustrative purposes only, hormones and hormone precursors, such as, for example, thyroid-stimulating hormone, follicle-stimulating hormone, luteinizing hormone, prolactin, growth hormone, adrenocorticotropic hormone, growth hormone-releasing hormone, corticotropin-releasing hormone, somatostatin, calcitonin, parathyroid hormone, human chorionic gonadotropin, insulin, glucagon, somatostatin, erythropoietin, atrial-natriuretic peptide, gastrin, secretin, cholecystokinin, somatostatin, neuropeptides, insulin-like growth factor-1, angiotensinogen, thrombopoietin and leptin; enzymes, such as, for example, oxidoreductases such as, for example, dehydrogenases, oxidases, reductases and catalases; transferases such as, for example, acetyltransferases, methylases, protein kinases and phosphatases; hydrolases including proteases, nucleases and phosphatases such as, for example, alkaline phosphatase or phytase; lyases including decarboxylases and aldolases; isomerases, such as, for example, epimerases and racemases; and ligases such as, for example, peptide synthases, aminoacyl-tRNA synthetases, DNA ligases and RNA ligases; cell toxins such as, for example, barnase; cell surface proteins such as, for example, transport proteins and receptor proteins; intracellular proteins such as, for example, proteins associated with intracellular signaling such as G-proteins and associated receptors, proteins associated with intracellular transport; structural proteins; reporter proteins such as, for example, beta-galactosidase and fluorescent proteins such as a green fluorescent protein; proteins conferring disease resistance, such as, for example, a viral coat protein polypeptide; antibodies, such as, for example, a "plantibody" (Gibbs, W W. *Scientific American* 277: 44, 1997), and numerous other proteins and polypeptides. The polypeptide can comprise, for example, a naturally occurring amino acid sequence, or conservative amino acid substitutions, deletions, or additions thereof which do not destroy the polypeptide's activity. Thus, the polypeptide can also comprise additional sequences, such as, for example, a leader sequence for cell secretion; a target sequence for a biotinylation reaction catalyzed by a biotin ligase; a polyhistidine sequence for purification on a heavy metal ion column such as, for example, a zinc ion column; an epitope tag, such as, for example, a FLAG sequence or a myc epitope tag; and a protease recognition site, such as, for example, an enterokinase recognition site. The DNA sequence comprising an anti-sense coding sequence for a heterologous polypeptide can comprise an artificial sequence or a naturally occurring DNA sequence. A DNA sequence encoding a polypeptide can encode translation codons that reflect the preferred codon usage of a host cell or organism. For example, if the host cell or organism species is *Nicotiana benthamiana*, a codon usage table can be used to select codons or their complements in designing an artificial DNA sequence or modifying a naturally occurring DNA sequence. It is expected that use of preferred codons in a coding sequence will lead to higher efficiency of translation of a transgene in a transgenic cell or organism. The DNA sequence comprising an antisense coding sequence for a heterologous polypeptide can further comprise one or more antisense introns, at least one antisense translation termination codon, and a transcription termination signal.

The DNA sequence complementary to an IRES can comprise a sequence complementary to any known IRES. The IRES can be, for example, any IRES known in the art to function to support internal ribosomal entry of an RNA in a eukaryotic cell. The IRES, therefore, may derive from any number of different viruses, animals, plants, or eukaryotic microorganisms, or may be an artificial IRES. Non-limiting examples of an IRES that can be used in the invention include those retrievable from an internet database (Bonnal et al., *Nucleic Acids Res.* 31: 427-428, 2003). Non-limiting examples of an IRES include a picornavirus IRES (Jang et al, *Enzyme* 44: 292-309, 1990; Roberts et al., *RNA* 4: 520-529, 1998), a foot-and-mouth disease virus IRES (Kuhn et al., *J. Virol.* 64: 4625-4631, 1990); an encephalomyocarditis virus IRES (Evstafieva et al., *Nucleic Acids Res.* 19: 665-671, 1991), a hepatitis A virus IRES (Brown et al., *J. Virol.* 65: 5828-5838, 1991), a hepatitis C virus IRES (Tsukiyama-Kohara et al., *J. Virol.* 66: 1476-1483, 1992), a human rhinovirus IRES (Borman et al., *Virology* 188: 685-696, 1992), a poliovirus IRES (Haller et al, *J. Virol.* 66: 5075-5086, 1992; Klinck et al., *Nucleic Acids Res.* 25: 2129-2137, 1997), a swine vesicular disease virus IRES (Chen et al., *J. Virol.* 67: 2142-2148, 1993), a turnip mosaic potyvirus IRES (Basso et al., *J. Gen. Virol.* 75: 3157-3165, 1994), a human fibroblast growth factor 2 mRNA IRES (Vagner et al., *Mol. Cell. Biol.* 15: 35-44, 1995), a pestivirus IRES (Poole et al., *Virology* 206: 750-754, 1995), a Leishmania RNA virus IRES (Maga et al., *Mol. Cell. Biol.* 15: 4884-4889, 1995), a Moloney murine leukemia virus IRES (Vagner S, *J. Biol. Chem.* 270: 20376-20383, 1995), a human rhinovirus 14 IRES (Rojas-Eisenring et al., *J. Virol.* 1995 69: 6819-6824, 1995), aphthovirus IRES (Martinez-Salas et al., *J. Virol.* 70: 992-998, 1996), a human immunoglobulin heavy chain binding protein (BiP) mRNA IRES (Le et al., *Nucleic Acids Res.* 25: 362-369, 1997), a *Drosophila* Antennapedia mRNA IRES (Le et al., *Nucleic Acids Res.* 25: 362-369, 1997), a human fibroblast growth factor 2 (FGF-2) mRNA IRES (Le et al., *Nucleic Acids Res.* 25: 362-369, 1997), a hepatitis G virus IRES (Pickering et al., *J. Viral. Hepat.* 4: 175-184, 1997), a tobamovirus IRES (Ivanov et al., *Virology* 232: 32-43, 1997), a vascular endothelial growth factor mRNA IRES (Stein et al., *Mol. Cell Biol.* 18: 3112-3119, 1998), a Coxsackie B group virus IRES (Carthy et al., Clin. Exp. Pharmacol. Physiol. 24: 997-1003, 1997), a c-myc protooncogene mRNA IRES (Nanbru et al., *J. Biol. Chem.* 272: 32061-32066, 1997; Nanbru et al., Oncogene 20:4270-4280, 2001), a human MYT2 mRNA IRES (Kim et al., *Mol. Cell. Neurosci.* 12:119-140, 1998), a human parechovirus type 1 virus IRES (Ghazi et al., *J. Gen. Virol.* 79: 2641-2650, 1998), a human parechovirus type 2 virus IRES (Ghazi et al., *J. Gen. Virol.* 79: 2641-2650, 1998), a eukaryotic initiation factor 4GI mRNA IRES (Johannes et al., RNA 4: 1500-1513, 1998), a Plautia stali intestine virus IRES (Sasaki et al., *J. Virol,* 73: 1219-1226, 1999), a Theiler's murine encephalomyelitis virus IRES (Yamasaki et al., *J. Virol.* 73: 8519-8526, 1999), a bovine enterovirus IRES (Zell et al., *J. Gen. Virol.* 80: 2299-2309, 1999), a connexin 43 mRNA IRES (Schiavi et al., *FEBS Lett.* 464: 118-122, 1999), a homeodomain protein Gtx mRNA IRES (Chappell et al., *Proc. Natl. Acad. Sci. USA* 97: 1536-1541, 2000), an AML1 transcription factor mRNA IRES (Pozner et al., *Mol. Cell.* Biol. 20: 2297-2307, 2000), an NF-kappa B repressing factor mRNA IRES (Oumard et al., *Mol. Cell.* Biol. 20: 2755-2759, 2000), an X-linked inhibitor of apoptosis (XIAP) mRNA IRES (Holcik et al., *Mol. Cell. Biol.* 20: 4648-4657, 2000), a cricket paralysis virus RNA IRES (Wilson et al., *Mol. Cell. Biol.* 20: 4990-4999, 2000), a p58(PITSLRE) protein kinase mRNA IRES (Cornelis et al. *Mol. Cell.* 5: 597-605, 2000), an ornithine decarboxylase mRNA IRES (Pyronnet et al., *Mol. Cell.* 5: 607-616, 2000), a connexin-32 mRNA IRES (Hudder et al., *J. Biol. Chem.* 275. 34586-34591, 2000), a bovine viral diarrhea virus IRES (Sanderbrand et al., *Vet. Microbiol.* 77. 215-227, 2000), an insulin-like growth factor I receptor mRNA IRES (Giraud et al., *J. Biol. Chem.* 276: 5668-5675, 2001), a human immunodeficiency virus type 1 gag gene IRES (Buck et al., *J. Virol.* 75: 181-191, 2001), a classical swine fever virus IRES (Kolupaeva et al., *RNA* 6: 1791-1807, 2000), a Kaposi's sarcoma-associated herpesvirus IRES (Grundhoff et al., *J. Virol.* 75. 1857-1863), a short IRES selected from libraries of random oligonucleotides (Owens et al., *Proc. Natl. Acad. Sci. USA* 98: 1471-1476, 2001), 2001; Bieleski et al., *J. Virol.* 75: 1864-1869, 2001), a Jembrana disease virus IRES (Metharom et al., *Vet. Microbiol.* 80: 9-22, 2001), an apoptotic protease-activating factor 1 mRNA IRES (Mitchell et al., Mol. Cell. Biol. 21: 3364-3374, 2001), a Rhopalosiphum padi virus IRES (Woolaway et al., *J. Virol.* 75: 10244-10249, 2001), a cationic amino acid transporter mRNA IRES (Fernandez et al., *J. Biol. Chem.* 277: 11780-11787, 2002), a human insulin-like growth factor II leader 2 mRNA IRES (Pedersen et al., *Biochem. J.* 363: 37-44, 2002), a giardiavirus IRES (Garlapati et al., *RNA* 8: 601-611, 2002), a Smad5 mRNA IRES (Shiroki et al., *Nucleic Acids Res.* 30: 2851-2861, 2002), a porcine teschovirus-1 talfan IRES (Kaku et al., *J. Virol.* 76: 11721-11728, 2002), a *Drosophila* Hairless mRNA IRES (Maier et al., *Proc. Natl. Acad. Sci. USA* 99:15480-15485, 2002), an hSNM1 mRNA IRES (Zhang et al., *DNA Repair* (*Amst*) 1: 379-390, 2002), a Cbfa1/Runx2 mRNA IRES (Xiao et al., *J. Cell Biochem.* 88: 493-505, 2003), an Epstein-Barr virus IRES (Isaksson et al., Oncogene 22: 572-581, 2003), a hibiscus chlorotic ringspot virus IRES (Koh et al., *J. Biol. Chem. in press*), a rat pituitary vasopressin V1b receptor mRNA IRES (Aguilera et al., *J. Mol. Endocrinol.* 30: 99-108, 2003), and a human hsp70 mRNA IRES (Rubtsova et al, J. Biol. Chem. in press).

In preferred embodiments, the IRES can be the picornavirus IRES, such as, for example, the encephalomyocarditis virus IRES comprised by plasmid pIRES (BD Biosciences Clontech, Palo Alto, Calif.). A DNA copy of the picornavirus internal ribosome entry site can comprise, for example, the sequence:

```
                                         (SEQ ID NO: 4)
AATTCCGCCCCTCTCCCTCCCCCCCCCCTAACGTTACTGGCCGAAGCCGC

TTGGAATAAGGCCGGTGTGCGTTTGTCTATATGTGATTTTCCACCATATT

GCCGTCTTTTGGCAATGTGAGGGCCCGGAAACCTGGCCCTGTCTTCTTGA
```

-continued

```
CGAGCATTCCTAGGGGTCTTTCCCCTCTCGCCAAAGGAATGCAAGGTCTG

TTGAATGTCGTGAAGGAAGCAGTTCCTCTGGAAGCTTCTTGAAGACAAAC

AACGTCTGTAGCGACCCTTTGCAGGCAGCGGAACCCCCCACCTGGCGACA

GGTGCCTCTGCGGCCAAAAGCCACGTGTATAAGATACACCTGCAAAGGCG

GCACAACCCCAGTGCCACGTTGTGAGTTGGATAGTTGTGGAAAGAGTCAA

ATGGCTCTCCTCAAGCGTATTCAACAAGGGGCTGAAGGATGCCCAGAAGG

TACCCCATTGTATGGGATCTGATCTGGGGCCTCGGTGCACATGCTTTACA

TGTGTTTAGTCGAGGTTAAAAAAACGTCTAGGCCCCCCGAACCACGGGGA

CGTGGTTTTCCTTTGAAAAACACGATGATAA.
```

An RNA copy of the IRES can comprise, for example, the sequence:

```
                                         (SEQ ID NO: 5)
AAUUCCGCCCCUCUCCCUCCCCCCCCCCUAACGUUACUGGCCGAAGCCGC

UUGGAAUAAGGCCGGUGUGCGUUUGUCUAUAUGUGAUUUUCCACCAUAUU

GCCGUCUUUUGGCAAUGUGAGGGCCCGGAAACCUGGCCCUGUCUUCUUGA

CGAGCAUUCCUAGGGGUCUUUCCCCUCUCGCCAAAGGAAUGCAAGGUCUG

UUGAAUGUCGUGAAGGAAGCAGUUCCUCUGGAAGCUUCUUGAAGACAAAC

AACGUCUGUAGCGACCCUUUGCAGGCAGCGGAACCCCCCACCUGGCGACA

GGUGCCUCUGCGGCCAAAAGCCACGUGUAUAAGAUACACCUGCAAAGGCG

GCACAACCCCAGUGCCACGUUGUGAGUUGGAUAGUUGUGGAAAGAGUCAA

AUGGCUCUCCUCAAGCGUAUUCAACAAGGGGCUGAAGGAUGCCCAGAAGG

UACCCCAUUGUAUGGGAUCUGAUCUGGGGCCUCGGUGCACAUGCUUUACA

UGUGUUUAGUCGAGGUUAAAAAAACGUCUAGGCCCCCCGAACCACGGGGA

CGUGGUUUUCCUUUGAAAAACACGAUGAUAA.
```

A DNA complementary to the IRES can comprise, for example, the sequence:

```
                                         (SEQ ID NO: 6)
TTATCATCGTGTTTTTCAAAGGAAAACCACGTCCCCGTGGTTCGGGGGGC

CTAGACGTTTTTTTAACCTCGACTAAACACATGTAAAGCATGTGCACCGA

GGCCCCAGATCAGATCCCATACAATGGGGTACCTTCTGGGCATCCTTCAG

CCCCTTGTTGAATACGCTTGAGGAGAGCCATTTGACTCTTTCCACAACTA

TCCAACTCACAACGTGGCACTGGGGTTGTGCCGCCTTTGCAGGTGTATCT

TATACACGTGGCTTTTGGCCGCAGAGGCACCTGTCGCCAGGTGGGGGGTT

CCGCTGCCTGCAAAGGGTCGCTACAGACGTTGTTTGTCTTCAAGAAGCTT

CCAGAGGAACTGCTTCCTTCACGACATTCAACAGACCTTGCATTCCTTTG

GCGAGAGGGGAAAGACCCCTAGGAATGCTCGTCAAGAAGACAGGGCCAGG

TTTCCGGGCCCTCACATTGCCAAAAGACGGCAATATGGTGGAAAATCACA

TATAGACAAACGCACACCGGCCTTATTCCAAGCGGCTTCGGCCAGTAACG

TTAGGGGGGGGGGAGGGAGAGGGGCGGAATT.
```

An RNA copy of the complement of the IRES can comprise, for example, the sequence:

(SEQ ID NO: 7)

```
UUAUCAUCGUGUUUUUCAAAGGAAAACCACGUCCCCGUGGUUCGGGGGGC
CUAGACGUUUUUUUAACCUCGACUAAACACAUGUAAAGCAUGUGCACCGA
GGCCCCAGAUCAGAUCCCAUACAAUGGGGUACCUUCUGGGCAUCCUUCAG
CCCCUUGUUGAAUACGCUUGAGGAGAGCCAUUUGACUCUUUCCACAACUA
UCCAACUCACAACGUGGCACUGGGGUUGUGCCGCCUUUGCAGGUGUAUCU
UAUACACGUGGCUUUUGGCCGCAGAGGCACCUGUCGCCAGGUGGGGGGUU
CCGCUGCCUGCAAAGGGUCGCUACAGACGUUGUUUGUCUUCAAGAAGCUU
CCAGAGGAACUGCUUCCUUCACGACAUUCAACAGACCUUGCAUUCCUUUG
GCGAGAGGGGAAAGACCCCUAGGAAUGCUCGUCAAGAAGACAGGGCCAGG
UUUCCGGGCCCUCACAUUGCCAAAAGACGGCAAUAUGGUGGAAAAUCACA
UAUAGACAAACGCACACCGGCCUUAUUCCAAGCGGCUUCGGCCAGUAACG
UUAGGGGGGGGGGAGGGAGAGGGGCGGAAUU.
```

The 3' UTR of the transgene can be a DNA copy of any known positive strand single-stranded RNA 3' UTR, no DNA stage. The 3' UTR sequence can be that of any known sequence of a positive strand single-stranded RNA virus, preferably a 3' UTR of a positive strand single-stranded RNA virus having no DNA stage, such as, for example a 3' UTR of a positive strand single-stranded RNA virus having no DNA stage selected from the group consisting of Aconitum latent virus, Acute bee paralysis virus, Acyrthosiphon pisum virus, Aichi virus, Alfalfa mosaic virus, Alkhurma virus, American plum line pattern virus, Aphid lethal paralysis virus, Apoi virus, Apple chlorotic leaf spot virus, Apple latent spherical virus, Apple mosaic virus, Apple stem grooving virus, Apple stem pitting virus, Artichoke mottled crinkle virus, Aura virus, Avian encephalomyelitis virus, Avian infectious bronchitis virus, Avian nephritis virus, Bacteriophage AP205, Bacteriophage M11, Bacteriophage SP, Bamboo mosaic virus, Banana mild mosaic virus, Barley mild mosaic virus, Barley stripe mosaic virus, Barley yellow dwarf virus-GAV, Barley yellow dwarf virus-MAV, Barley yellow dwarf virus-PAV, Barley yellow dwarf virus-PAS, Barley yellow mosaic virus, Barmah Forest virus, Bean common mosaic necrosis virus, Bean common mosaic virus, Bean leafroll virus, Bean pod mottle virus, Bean yellow mosaic virus, Beet black scorch virus, Beet chlorosis virus, Beet mild yellowing virus, Beet necrotic yellow vein virus, Beet ringspot virus, Beet soil-borne mosaic virus, Beet soil-borne virus, Beet virus Q, Beet western yellows ST9 associated virus, Beet western yellows virus, Beet yellows virus, Black beetle virus, Black queen cell virus, Blackcurrant reversion virus, Blueberry scorch virus, Boolarra virus, Botrytis virus F, Bovine coronavirus, Bovine enterovirus, Bovine kobuvirus, Bovine viral diarrhea virus genotype 2, Broad bean mottle virus, Broad bean necrosis virus, Broad bean wilt virus 2, Brome mosaic virus, Brome streak mosaic virus, Cactus virus X, Calicivirus strain NB, Canine calicivirus, Cardamine chlorotic fleck virus, Carnation Italian ringspot virus, Carnation mottle virus, Carnation ringspot virus, Carrot mottle mimic virus, Cassava common mosaic virus, Cell fusing agent virus, Cereal yellow dwarf virus-RPS, Cereal yellow dwarf virus-RPV, Chayote mosaic tymovirus, Cherry green ring mottle virus, Cherry mottle leaf virus, Cherry necrotic rusty mottle virus, Cherry virus A, Chikungunya virus, Chinese wheat mosaic virus, Citrus leaf blotch virus, Citrus leaf rugose virus, Citrus tristeza virus, Clover yellow mosaic virus, Clover yellow vein virus, Cocksfoot mottle virus, Cocksfoot streak virus, Cowpea aphid-borne mosaic virus, Cowpea chlorotic mottle virus, Cowpea mosaic virus, Cowpea mottle virus, Cowpea severe mosaic virus, Cricket paralysis virus, Crucifer tobamovirus, Cryphonectria parasitica mitovirus 1-NB631, Cucumber Bulgarian virus, Cucumber fruit mottle mosaic virus, Cucumber green mottle mosaic virus, Cucumber mosaic virus, Cucumber necrosis virus, Cucumber yellows virus, Cucurbit aphid-borne yellows virus, Cucurbit yellow stunting disorder virus, Cycas necrotic stunt virus, Cymbidium mosaic virus, Cymbidium ringspot virus, Dasheen mosaic virus, Deer tick virus, Dengue virus, Drosophila C virus, Eastern equine encephalitis virus, Eggplant mosaic virus, Elm mottle virus, Encephalomyocarditis virus, Enterobacteria phage fr, Enterobacteria phage GA, Enterobacteria phage KU1, Enterobacteria phage MX1, Enterobacteria phage NL95, Enterobacterio phage MS2, Enterovirus Yanbian 96-83csf, Epinephelus tauvina nervous necrosis virus, Equine arteritis virus, Equine rhinitis A virus, Equine rhinitis B virus, Equine rhinovirus 3, Erysimum latent virus, Euprosterna elaeasa virus, European brown hare syndrome virus, Feline calicivirus, Flock house virus, Foot-and-mouth disease virus C, Foot-and-mouth disease virus O, Foot-and-mouth disease virus SAT 2, Foxtail mosaic virus, Galinsoga mosaic virus, Garlic latent virus, Garlic virus A, Garlic virus C, Garlic virus E, Garlic virus X, Grapevine chrome mosaic virus, Grapevine fanleaf virus, Grapevine fleck virus, Grapevine leafroll-associated virus 3, Grapevine rootstock stem lesion associated virus, Grapevine virus A, Grapevine virus B, Groundnut rosette virus, Helicoverpa armigera stunt virus, Hepatitis A virus, Hepatitis C virus, Hepatitis E virus, Hepatitis G virus, Hepatitis GB virus A, Hepatitis GB virus B, Hepatitis GB virus C, Hibiscus chlorotic ringspot virus, Himetobi P virus, Hop latent virus, Human astrovirus, Human coronavirus 229E, Human echovirus 1, Human enterovirus A, Human enterovirus B, Human enterovirus C, Human enterovirus D, Human enterovirus E, Human parechovirus 2, Human rhinovirus 89, Human rhinovirus B, Igbo Ora virus, Indian citrus ringspot virus, Indian peanut clump virus, Infectious flacherie virus, Japanese encephalitis virus, Japanese iris necrotic ring virus, Japanese yam mosaic virus, Johnsongrass mosaic virus, Kashmir bee virus, Kennedya yellow mosaic virus, Kyuri green mottle mosaic virus, Lactate dehydrogenase-elevating virus, Langat virus, Leek white stripe virus, Leek yellow stripe potyvirus, Lettuce infectious yellows virus, Lettuce mosaic virus, Little cherry virus 1, Ljungan virus, Louping ill virus, Lucerne transient streak virus, Maize chlorotic dwarf virus, Maize chlorotic mottle virus, Maize dwarf mosaic virus, Maize rayado fino virus, Mayaro virus, Melon necrotic spot virus, Mink astrovirus, Modoc virus, Montana myotis leukoencephalitis virus, Murine hepatitis virus, Murray Valley encephalitis virus, Mushroom bacilliform virus, Narcissus mosaic virus, Nodamura virus, Norwalk virus, Nudaurelia capensis beta virus, O'nyong-nyong virus, Oat blue dwarf virus, Oat chlorotic stunt virus, Oat golden stripe virus, Oat mosaic virus, Obuda pepper virus, Odontoglossum ringspot virus, Olive latent virus 1, Olive latent virus 2, Ononis yellow mosaic virus, Ophiostoma mitovirus 3a, Ophiostoma novo-ulmi mitovirus 4-Ld, Ophiostoma novo-ulmi mitovirus 5-Ld, Ophiostoma novo-ulmi mitovirus 6-Ld, Ovine astrovirus, Oyster mushroom spherical virus, Panicum mosaic virus, Papaya mosaic virus, Papaya ringspot virus, Paprika mild mottle virus, Pariacoto virus, Parsnip yellow fleck virus, Patchouli mild mosaic virus, Pea early browning virus, Pea enation mosaic virus-1, Pea enation mosaic virus-2, Pea seed-borne mosaic virus, Peanut clump virus, Peanut mottle virus, Peanut stunt virus, Pear latent virus, Pelargonium zonate spot virus, Pepino mosaic virus, Pepper mild mottle virus, Pepper mottle virus, Pepper ringspot virus, Perina nuda picorna-like virus, Peru tomato mosaic virus, Pestivirus Giraffe-1, Pestivirus Reindeer-1, Pestivirus type 1, Pestivirus type 2, Pestivirus type 3, Physalis mottle virus, Plantago asiatica mosaic virus, Plautia stali intestine virus, Plum pox virus, Poinsettia mosaic virus, Poliovirus, Porcine enteric calicivirus, Porcine enterovirus A, Porcine enterovirus B, Porcine epidemic diarrhea virus, Porcine reproductive and respiratory syndrome virus, Porcine teschovirus 1, Potato aucuba mosaic virus, Potato leafroll virus, Potato mop-top virus, Potato virus A, Potato virus M, Potato virus V, Potato virus X, Potato virus Y, Pothos latent virus, Powassan virus, Prunus necrotic ringspot virus, *Pseudomonas* phage PP7, Rabbit hemorrhagic disease virus, Raspberry bushy dwarf virus, Red clover mottle virus, Red clover necrotic mosaic virus, *Rhopalosiphum padi* virus, Ribgrass mosaic virus, Rice tungro spherical virus, Rice yellow mottle virus, Rio Bravo virus, Ross River virus, Rubella virus, Rupestris stem pitting associated virus-1, Ryegrass mosaic virus, Ryegrass mottle virus, Sacbrood virus, Saccharomyces cerevisiae narnavirus 20S RNA, Saccharomyces cerevisiae narnavirus 23S RNA, Saguaro cactus virus, Salmon pancreas disease virus, SARS coronavirus, Satsuma dwarf virus, Scallion mosaic virus, Scallion virus X, Semliki forest virus, Sesbania mosaic virus, Shallot virus X, Simian hemorrhagic fever virus, Simian picornavirus 1, Sindbis virus, Sleeping disease virus, Soil-borne cereal mosaic virus, Soil-borne wheat mosaic virus, Sorghum chlorotic spot virus, Sorghum mosaic virus, Southern bean mosaic virus, Southern cowpea mosaic virus, Soybean dwarf virus, Soybean mosaic virus, Spinach latent virus, Spring beauty latent virus, Squash mosaic virus, Strawberry mild yellow edge virus, Strawberry mottle virus, Striped Jack nervous necrosis virus, Subterranean clover mottle virus, Sugarcane mosaic virus, Sugarcane striate mosaic associated virus, Sugarcane yellow leaf virus, Sweet clover necrotic mosaic virus, Sweet potato chlorotic stunt virus, Sweet potato feathery mottle virus, Sweet potato mild mottle virus, Tamana bat virus, Taura syndrome virus, Theilovirus, Tick-borne encephalitis virus, Tobacco bushy top virus, Tobacco etch virus, Tobacco mild green mosaic virus, Tobacco mosaic virus, Tobacco necrosis virus A, Tobacco necrosis virus D, Tobacco rattle virus, Tobacco streak virus, Tobacco vein mottling virus, Tomato aspermy virus, Tomato black ring virus, Tomato bushy stunt virus, Tomato mosaic virus, Tomato ringspot virus, Transmissible gastroenteritis virus, Triatoma virus, Tulare apple mosaic virus, Tulip virus X, Turkey astrovirus, Turnip crinkle virus, Turnip mosaic virus, Turnip rosette virus, Turnip vein-clearing virus, Turnip yellow mosaic virus, Turnip yellows virus, Venezuelan equine encephalitis virus, Vesicular exanthema of swine virus, Walrus calicivirus, West Nile virus, Western equine encephalomyelitis virus, Wheat streak mosaic virus, Wheat yellow mosaic virus, White clover mosaic, virus, Wild potato mosaic virus, Yam mosaic virus, Yellow fever virus, Youcai mosaic virus, Zucchini green mottle mosaic virus and Zucchini yellow mosaic virus. Preferably, the 3' UTR is that of a positive strand single-stranded plant virus having no DNA stage, and can be, for example, a 3' UTR of a Cowpea chlorotic mottle virus, a 3' UTR of a Brome mosaic bromovirus, a 3' UTR of a Lettuce mosaic virus, or a 3' UTR of a Cucumber mosaic virus.

Preferably, the 3' UTR is the 3' UTR of a Cowpea chlorotic mottle virus. A DNA copy of a Cowpea chlorotic mottle virus 3' UTR can comprise, for example, the sequence:

```
                                                (SEQ ID NO: 8)
AGTGCCCGCTGAAGAGCGTTACACTAGTGTGGCCTACTTGAAGGCTAGTT

ATAACCGTTTCTTTAAACGGTAATCGTTGTTGAAACGTCTTCCTTTTACA

AGAGGATTGAGCTGCCCTTGGGTTTTACTCCTTGAACCCTTCGGAAGAAC

TCTTTGGAGTTCGTACCAGTACCTCACATAGTGAGGTAATAAGACTGGTG

GGCAGCGCCTAGTCGAAAGACTAGGTGATCTCTAAGGAGACC.
```

An RNA copy of the 3' UTR can comprise, for example, the sequence:

```
                                                (SEQ ID NO: 9)
AGUGCCCGCUGAAGAGCGUUACACUAGUGUGGCCUACUUGAAGGCUAGUU

AUAACCGUUUCUUUAAACGGUAAUCGUUGUUGAAACGUCUUCCUUUUACA

AGAGGAUUGAGCUGCCCUUGGGUUUUACUCCUUGAACCCUUCGGAAGAAC

UCUUUGGAGUUCGUACCAGUACCUCACAUAGUGAGGUAAUAAGACUGGUG

GGCAGCGCCUAGUCGAAAGACUAGGUGAUCUCUAAGGAGACC.
```

A DNA copy of the complement of the 3' UTR can comprise, for example, the sequence:

```
                                               (SEQ ID NO: 10)
GGTCTCCTTAGAGATCACCTAGTCTTTCGACTAGGCGCTGCCCACCAGTC

TTATTACCTCACTATGTGAGGTACTGGTACGAACTCCAAAGAGTTCTTCC

GAAGGGTTCAAGGAGTAAAACCCAAGGGCAGCTCAATCCTCTTGTAAAAG

GAAGACGTTTCAACAACGATTACCGTTTAAAGAAACGGTTATAACTAGCC

TTCAAGTAGGCCACACTAGTGTAACGCTCTTCAGCGGGCACT.
```

An RNA copy of the complement of the 3' UTR can comprise, for example, the sequence:

```
                                               (SEQ ID NO: 11)
GGUCUCCUUAGAGAUCACCUAGUCUUUCGACUAGGCGCUGCCCACCAGUC

UUAUUACCUCACUAUGUGAGGUACUGGUACGAACUCCAAAGAGUUCUUCC

GAAGGGUUCAAGGAGUAAAACCCAAGGGCAGCUCAAUCCUCUUGUAAAAG

GAAGACGUUUCAACAACGAUUACCGUUUAAAGAAACGGUUAUAACUAGCC

UUCAAGUAGGCCACACUAGUGUAACGCUCUUCAGCGGGCACU.
```

In another aspect, the invention is directed to a host cell comprising the recombinant DNA transgene. The host cell can be any eukaryotic cell, preferably a plant cell. The plant host cell can be a dicotyledonous plant host cell or a monocotyledonous plant host cell. The plant host cell can be a crop plant host cell. In preferred embodiments, the plant cell is a dicotyledonous plant host cell, preferably a *Nicotiana* plant host cell, more preferably a *Nicotiana bentamiana* host plant cell.

In another embodiment, the invention is directed to a recombinant RNA molecule, wherein the recombinant RNA molecule comprises, in 5' to 3' direction, an anti-sense coding sequence for a heterologous polypeptide, an anti-sense IRES, and a 3' UTR of a positive strand single-stranded RNA virus. The anti-sense coding sequence for a heterologous polypeptide of the recombinant RNA can correspond in sequence to the anti-sense coding sequence for a heterologous polypeptide of the recombinant DNA transgene described above.

The methods disclosed in the present invention comprise inoculating, infecting or tranfecting a transgenic host cell or organism with a positive strand single-stranded RNA virus having no DNA stage in order to stimulate or activate the formation of a complementary strand of the transgene. The inoculating, infecting or transfecting can be by any inoculating, infection or transfection method known in the art. The positive strand single-stranded RNA virus having no DNA stage that can be used to stimulate or activate the formation of the RNA complement of the recombinant RNA can be a plant virus or an animal virus, a portion thereof, or a nucleic acid thereof. Non-limiting examples of single-stranded RNA positive-strand plant viruses having no DNA stage include: Allexivirus, such as, for example, Garlic virus A, Garlic virus B, Garlic virus C, Garlic virus D, Garlic virus E, Garlic virus X, Shallot virus X; Benyvirus, such as, for example, Beet necrotic yellow vein virus, Beet soil-borne mosaic virus (BSBMV); Bromoviridae, such as, for example, Alfamovirus, such as, for example, Alfalfa mosaic virus; Bromovirus, such as, for example, Broad bean mottle virus, Brome mosaic virus, Cowpea chlorotic mottle virus, Spring beauty latent virus; Cucumovirus, such as, for example, Cucumber mosaic virus (cucumber mosaic cucumovirus), Peanut stunt virus, Tomato aspermy virus; Ilarvirus, such as, for example, American plum line pattern virus, Tobacco streak virus, Asparagus virus 2, Citrus leaf rugose virus, Citrus variegation virus, Elm mottle virus, Tulare apple mosaic virus, Apple mosaic virus, Prunus necrotic ringspot virus, Prune dwarf virus, Spinach latent virus, Lilac ring mottle virus, Hydrangea mosaic virus 8; Oleavirus, such as, for example, Olive latent virus 2, Pelargonium zonate spot virus; Caliciviridae, such as, for example, Capillovirus, such as, for example, Apple stem grooving virus, Citrus tatter leaf virus, Cherry virus A; Carlavirus, such as, for example, Aconitum latent virus, Alfalfa latent carlavirus, Blueberry scorch virus, Carnation latent virus, Chrysanthemum virus B, Cowpea mild mottle virus, Garlic common latent virus, Garlic latent virus, Garlic latent virus E29-6, Garlic virus 1, Helenium virus S, Hop latent virus, Hop mosaic virus, Kalanchoe latent virus, Lily latent virus (LiLV), Lily symptomless virus (LSV), Narcissus carlavirus, Pea streak virus, Poplar mosaic virus, Poplar mosaic virus (ATCC PV257), Potato latent virus, Potato rough dwarf virus, Potato virus M, Potato virus S, Shallot latent virus, Sugarcane striate mosaic virus, unidentified Verbena-infecting Carlavirus; Closteroviridae, such as, for example, Ampelovirus, such as, for example, Grapevine leafroll-associated virus 1, Grapevine leafroll-associated virus 3, Grapevine leafroll-associated virus 4, Grapevine leafroll-associated virus 5, Grapevine leafroll-associated virus 6, Grapevine leafroll-associated virus 8, little cherry virus 2, Pineapple mealybug wilt-associated virus 1, Pineapple mealybug wilt-associated virus 2, Plum bark necrosis stem pitting virus; Closterovirus, such as, for example, Apricot stem pitting associated virus, Beet yellow stunt virus, Beet yellows virus, Citrus tristeza virus, Grapevine leafroll-associated virus 2, Grapevine rootstock stem lesion associated virus, Olive leaf yellowing associated virus; Crinivirus, such as, for example, Beet pseudo-yellows virus, Cucumber yellows virus, Cucurbit yellow stunting disorder virus, Lettuce infectious yellows virus, Potato yellow vein virus, Strawberry pallidosis associated virus, Sweet potato chlorotic stunt virus, Tomato chlorosis virus, Tomato infectious chlorosis virus; unassigned species in the family Closteroviridae, such as, for example, Grapevine leafroll-associated virus 7, little cherry virus 1; Comoviridae, such as, for example, Comovirus, such as, for example, Andean potato mottle virus, Bean pod mottle virus, Bean rugose mosaic virus, Cowpea mosaic virus, Cowpea severe mosaic virus, Red clover mottle virus, Squash mosaic virus; Fabavirus, such as, for example, Broad bean wilt virus, Broad bean wilt virus 1, Broad bean wilt virus 2, Patchouli mild mosaic virus; Nepovirus, such as, for example, Apricot latent ringspot virus, Grapevine fanleaf virus, Arabis mosaic virus, Raspberry ringspot virus, Raspberry ringspot virus (strain S), Tobacco ringspot virus, Artichoke italian latent virus, Beet ringspot virus, Cycas necrotic stunt virus, Grapevine chrome mosaic virus, Olive latent ringspot virus, Tomato black ring virus, Blackcurrant reversion virus, Blueberry leaf mottle virus, Cherry leaf roll virus, Chicory yellow mottle virus, Peach rosette mosaic virus, Tomato ringspot virus, unclassified Comoviridae, such as, for example, Cherry rasp leaf virus; Foveavirus, such as, for example, African oil palm ringspot virus, Apple stem pitting virus, Banana mild mosaic virus, Cherry green ring mottle virus, Cherry necrotic rusty mottle virus, Peach asteroid spot virus, Peach sooty ringspot virus, Prunus mume foveavirus, Rupestris stem pitting-associated virus; Furovirus, such as, for example, Chinese wheat mosaic virus, Nicotiana velutina mosaic virus, Oat golden stripe virus, Soil-borne cereal mosaic virus, Soil-borne wheat mosaic virus, Sorghum chlorotic spot virus; Hordeivirus, such as, for example, Barley stripe mosaic virus, Lychnis ringspot virus, Poa semilatent virus; Idaeovirus, such as, for example, Raspberry bushy dwarf virus; Luteoviridae, such as, for example, Enamovirus, such as, for example, Pea enation mosaic virus; Luteovirus, such as, for example, Barley yellow dwarf virus, Bean leafroll virus, Carrot red leaf virus, Chickpea stunt disease associated virus, Groundnut rosette assistor virus, Soybean dwarf virus, Tobacco vein-distorting virus; Polerovirus, such as, for example, Beet chlorosis virus, Beet mild yellowing virus, Beet western yellows virus, Cereal yellow dwarf virus-RPS, Cereal yellow dwarf virus-RPV, Cucurbit aphid-borne yellows virus, Potato leafroll virus, Tobacco vein distorting polerovirus, Turnip yellows virus; Unassigned Luteoviridae, such as, for example, Sugarcane yellow leaf virus; Marafivirus, such as, for example, Bermuda grass etched-line virus, Maize rayado fino virus, Oat blue dwarf virus, Poinsettia mosaic virus; Pecluvirus, such as, for example, Indian peanut clump virus, such as, for example, Indian peanut clump virus D, Indian peanut clump virus H, Indian peanut clump virus L; Peanut clump virus, such as, for example, Peanut clump virus B, Peanut clump virus M, Peanut clump virus N, Peanut clump virus Ni; Pomovirus, such as, for example, Beet soil-borne virus, Beet virus Q, Broad bean necrosis virus, Potato mop-top virus; Potexvirus, such as, for example, Alternanthera potexvirus, Bamboo mosaic virus, Cactus virus X, Cassaya common mosaic virus, Clover yellow mosaic virus, Cymbidium mosaic virus, Foxtail mosaic virus, Hydrangea ringspot virus, Lily virus X, Narcissus mosaic virus, Papaya mosaic virus, Pepino mosaic virus, Plantago asiatica mosaic potexvirus, Plantago asiatica mosaic virus, Potato aucuba mosaic virus, Potato virus X, Scallion virus X, Strawberry mild yellow edge virus, Tulip virus X, White clover mosaic virus; Potyviridae, such as, for example, Bymovirus, such as, for example, Barley mild mosaic virus, Barley yellow mosaic virus, Oat mosaic virus, Rice necrosis mosaic virus, Wheat spindle streak mosaic virus, Wheat yellow mosaic virus; Ipomovirus, such as, for example, Cassaya brown streak virus, Sweet potato mild mottle virus; Macluravirus, such as, for example, Maclura mosaic virus, such as, for example, Cardamom mosaic virus, Indian cardamom mosaic virus, Narcissus latent virus; Potyvirus, such as, for example, Alpinia mosaic virus, Apium virus Y, Artichoke latent potyvirus, Banana bract mosaic virus, Bean black root virus, Bean common mosaic necrosis virus; Bean common mosaic virus, such as, for example, Azuki bean mosaic virus, Blackeye cowpea mosaic virus, Dendrobium mosaic virus, Peanut stripe virus, Bean yellow mosaic virus, Beet mosaic virus, Brome streak mosaic potyvirus, Calanthe mild mosaic potyvirus, Carnation vein mottle virus, Carrot thin leaf virus, Carrot virus Y, Celery mosaic virus, Celery yellow mosaic virus, Ceratobium mosaic potyvirus, Chilli vein-banding mottle virus, Chinese narcissus potyvirus, Clitoria virus Y, Clover yellow vein virus, Cocksfoot streak virus, Colombian datura potyvirus, Cowpea aphid-borne mosaic virus, Crotalaria mosaic potyvirus, Cucurbit yellows-associated virus, Cypripedium virus Y, Dasheen mosaic virus, Dioscorea dumentorum virus, Diurus virus Y, Endive necrotic mosaic virus, Garlic mite-borne mosaic virus, Garlic mosaic virus, Garlic potyvirus 1, Garlic virus 2, Gloriosa stripe mosaic virus, Hibbertia virus Y, Iranian Johnson grass mosaic virus, Iris mild mosaic virus, Iris severe mosaic virus, Japanese hornwort mosaic virus, Japanese yam mosaic virus, Johnsongrass mosaic virus, Leek yellow stripe potyvirus, Lettuce mosaic virus, Lily mottle virus, Lycoris mild mottle virus, Maize dwarf mosaic virus, Moroccan watermelon mosaic virus, Narcissus late season yellow virus, Narcissus yellow stripe virus, Onion yellow dwarf virus, Ornithogalum mosaic virus, Ornithogalum virus 2, Ornithogalum virus 3, Papaya leaf-distortion mosaic potyvirus, Papaya ringspot virus, Passion fruit woodiness virus, Pea seed-borne mosaic virus, Peanut chlorotic blotch virus, Peanut mottle virus, Pennisetum flaccidum mosaic virus, Pepper mottle virus, Pepper severe mosaic virus, Pepper vein banding virus, Pepper yellow mosaic virus, Peru tomato mosaic virus, Petunia flower mottle virus, Pleione virus Y, Plum pox virus, Potato virus A, Potato virus V, Potato virus Y, Pterostylis virus Y, Rembrandt tulip-breaking virus, Rhopalanthe virus Y, Sarcochilus virus Y, Sesame mosaic potyvirus, Shallot potyvirus, Shallot yellow stripe virus, Sorghum mosaic virus, South African passiflora virus, Soybean mosaic virus, Sugarcane mosaic virus, Sugarcane streak mosaic virus, Sunflower chlorofic mottle virus, Sunflower chlorotic spot virus, Sunflower mosaic virus, Sweet potato feathery mottle virus, Sweet potato G virus, Sweet potato latent virus, Sweet potato mild speckling potyvirus, Sweet potato virus Y, Tamarillo mosaic virus, Tobacco etch virus, Tobacco vein banding mosaic virus, Tobacco vein mottling virus, Tuberose mild mosaic virus, Tulip band-breaking virus, Tulip breaking virus, Tulip mosaic virus, Tulip top-breaking virus, Turnip mosaic virus, Vanilla mosaic virus, Watermelon bud necrosis virus, Watermelon leaf mottle virus; Watermelon mosaic virus, such as, for example, Vanilla necrosis virus, Welsh onion yellow stripe virus, Wild potato mosaic virus, Wisteria vein mosaic virus, Yam mild mosaic virus, Yam mosaic virus, Zantedeschia mosaic virus, Zea mosaic virus, Zucchini yellow mosaic virus; Rymovirus, such as, for example, Agropyron mosaic virus, *Hordeum* mosaic virus, Oat necrotic mottle virus, Ryegrass mosaic virus; Tritimovirus, such as, for example, Brome streak mosaic virus, Wheat streak mosaic virus; unclassified Potyviridae, such as, for example, Chinese yam necrotic mosaic virus, Cucumber vein yellowing virus, Scallion mosaic virus, Spartina mottle virus, Tomato mild mottle virus; Sequiviridae, such as, for example, SDV-like viruses, such as, for example, Apple latent spherical virus, Citrus mosaic virus, Navel orange infectious mottling virus, Satsuma dwarf virus, Strawberry latent ringspot virus, Strawberry mottle virus; Sequivirus, such as, for example, Parsnip yellow fleck virus; Waikavirus, such as, for example, Maize chlorotic dwarf virus, Rice tungro spherical virus; Sobemovirus, such as, for example, Cocksfoot mottle virus, Lucerne transient streak virus, Rice yellow mottle virus, Ryegrass mottle virus, Sesbania mosaic virus, Southern bean mosaic virus, Southern cowpea mosaic virus, Subterranean clover mottle virus, Turnip rosette virus; Tetraviridae, such as, for example, Betatetravirus, such as, for example, Nudaurelia capensis beta virus; Omegatetravirus, such as, for example, Nudaurelia capensis omega virus; unclassified Tetraviridae, such as, for example, Helicoverpa armigera stunt virus, Providence virus, Thosea asigna virus; Tobamovirus, such as, for example, Chinese Rape Mosaic Virus, Crucifer tobamovirus, Cucumber fruit mottle mosaic virus, Cucumber green mottle mosaic virus, Frangipani mosaic virus, Hibiscus virus S, Kyuri green mottle mosaic virus, Obuda pepper virus, Odontoglossum ringspot virus, Paprika mild mottle virus, Pepper mild mottle virus, Ribgrass mosaic virus, Sunn-hemp mosaic virus, Tobacco mild green mosaic virus, Tobacco mosaic virus, Tomato mosaic virus, Turnip vein-clearing virus, Youcai mosaic virus, Zucchini green mottle mosaic virus; Tobravirus, such as, for example, Pea early browning virus, Pepper ringspot virus, Tobacco rattle virus; Tombusviridae, such as, for example, Aureusvirus, such as, for example, Pothos latent virus; Avenavirus, such as, for example, Oat chlorotic stunt virus; Carmovirus, such as, for example, Calibrachoa mottle virus, Cardamine chlorotic fleck virus, Carnation mottle virus, Cowpea mottle virus, Elderberry latent virus, Galinsoga mosaic virus, Hibiscus chlorotic ringspot virus, Japanese iris necrotic ring virus, Melon necrotic spot virus, Pelargonium flower break virus, Saguaro cactus virus, Turnip crinkle virus; Dianthovirus, such as, for example, Carnation ringspot virus, Dianthovirus RVX1, Red clover necrotic mosaic virus, Sweet clover necrotic mosaic virus; Machlomovirus, such as, for example, Maize chlorotic mottle virus; Necrovirus, such as, for example, Beet black scorch virus, Leek white stripe virus, Olive latent virus 1; Panicovirus, such as, for example, Panicum mosaic virus; Tombusvirus, such as, for example, Artichoke mottled crinkle virus, Carnation Italian ringspot virus, Cucumber Bulgarian virus, Cucumber necrosis virus, Cymbidium ringspot virus, Grapevine Algerian latent virus, Lettuce necrotic stunt virus, Moroccan pepper virus, Pear latent virus, Pelargonium leaf curl virus, Tomato bushy stunt virus; unclassified Tombusviridae, such as, for example, Cucumber leaf spot virus, Maize necrotic streak virus, Pelargonium chlorotic ring pattern virus, Pelargonium line pattern virus, Pelargonium ringspot virus; Trichovirus, such as, for example, Apple chlorotic leaf spot virus, Apricot trichovirus, Cherry mottle leaf virus, Grapevine berry inner necrosis virus, Peach mosaic virus, Potato trichovirus T; Tymovirus, such as, for example, Andean potato latent virus, Belladonna mottle virus, Cacao yellow mosaic virus, Chayote mosaic tymovirus, Clitoria yellow vein virus, Desmodium yellow mottle tymovirus, Dulcamara mottle virus, Eggplant mosaic virus, Erysimum latent virus, Kennedya yellow mosaic virus, Okra mosaic tymovirus, Ononis yellow mosaic virus, Passion fruit yellow mosaic virus, Petunia vein banding virus, Physalis mottle virus, Turnip yellow mosaic virus, Wild cucumber mosaic virus; Umbravirus, such as, for example, Carrot mottle mimic virus, Groundnut rosette virus, Pea enation mosaic virus-2, Tobacco bushy top virus, Tobacco mottle virus; Vitivirus, such as, for example, Grapevine virus A, Grapevine virus B, Grapevine virus D, Heracleum latent virus; unclassified single-stranded RNA positive-strand viruses, such as, for example, Acyrthosiphon pisum virus, Apricot latent virus, Beet western yellows ST9 associated virus, Botrytis virus F, Citrus leaf blotch virus, Euprosterna elaeasa virus, Grapevine fleck virus, Indian citrus ringspot virus, Oyster mushroom spherical virus, Pear vein yellows-associated virus, and Sugarcane striate mosaic associated virus.

Non-limiting examples of single-stranded RNA positive-strand animal viruses having no DNA stage include: Astroviridae, such as, for example, Astrovirus, such as, for example, Feline astrovirus, Human astrovirus, Mink astrovirus, Ovine astrovirus, Porcine astrovirus, Turkey astrovirus, Astrovirus sp., Avian nephritis virus; Caliciviridae, such as, for example, Lagovirus, such as, for example, European brown hare syndrome virus, Rabbit hemorrhagic disease virus, Norovirus, such as, for example, Bovine enteric calici-like virus, Maryland calicivirus 6, Minireovirus, Murine norovirus 1, Norwalk virus, such as, for example, Camberwell virus, Chiba virus, Chitta virus, Desert Shield virus, Hawaii calicivirus, Human calicivirus genogroup 1, Norwalk virus, Lordsdale virus, Maryland calicivirus 1, Norwalk-like virus, Norwalk-like virus genogroup 2, Small round structured virus, Snow Mountain virus, Southampton virus; Oyster norovirus, Saratoga calicivirus 7, Swine calicivirus, Sapovirus, such as, for example, Human calicivirus strain HuCV/Potsdam/2000/DEU, Manchester virus, Mink enteric calicivirus, Porcine enteric calicivirus, Sapporo virus, Toronto calicivirus 24, Vesivirus, such as, for example, Feline calicivirus, FCV-like Calicivirus, Unassigned Veriviruses, such as, for example, Canine calicivirus, Mink calicivirus; Walrus calicivirus, Vesicular exanthema of swine virus, such as, for example, Bovine calicivirus, Bovine Calicivirus Bos-2, Cetacean calicivirus, Primate calicivirus, Reptile calicivirus; San Miguel sea lion virus, such as, for example, San Miguel sea lion virus 13, San Miguel sea lion virus 2, San Miguel sea lion virus 6, San Miguel sea lion virus 1, San Miguel sea lion virus 4, Skunk calicivirus, Vesicular exanthema of swine virus A48, VESV-like calicivirus; unclassified Caliciviridae, such as, for example, Calicivirus strain CV23-OH, Calicivirus strain NB, Human calicivirus strain A141, Chiba virus, Chitta virus, Desert Shield virus, Hawaii calicivirus, Human calicivirus genogroup 1, Norwalk virus, Lordsdale virus, Maryland calicivirus 1, Norwalk-like virus, Norwalk-like virus genogroup 2, Small round structured virus, Snow Mountain virus, Southampton virus, Cricket paralysis-like viruses, such as, for example; Acute bee paralysis virus, Aphid lethal paralysis virus, Black queen cell virus, Cricket paralysis virus, Drosophila C virus, Himetobi P virus, Kashmir bee virus, Plautia stali intestine virus, Rhopalosiphum padi virus, Taura syndrome virus, Triatoma virus, Flaviviridae, such as, for example, Flavivirus (arboviruses group B), such as, for example, Cell fusing agent virus, Dengue virus group, Japanese encephalitis virus group, Modoc virus group, mosquito-borne viruses, Ntaya virus group, Rio Bravo virus group, tick-borne encephalitis virus group, Tyuleniy virus group, Uganda S virus group, Yellow fever virus group, unclassified Flavivirus, Hepacivirus, such as, for example, Hepatitis C virus; Pestivirus, such as, for example, Bovine viral diarrhea virus genotype 2 (BVDV-2), Pestivirus type 1, Pestivirus type 2, Pestivirus type 3, unclassified Pestivirus, unclassified Flaviviridae, such as, for example, Douroucouli hepatitis GB virus A, GBV-A-like virus, GBV-C/HGV group, Hepatitis GB virus A, Hepatitis GB virus B, Marmoset hepatitis GB virus A, Turkey meningoencephalitis virus, Nidovirales, such as, for example; Arteriviridae, such as, for example, Arterivirus, such as, for example, Equine arteritis virus, Lactate dehydrogenase-elevating virus, Porcine reproductive and respiratory syndrome virus, Lelystad virus, Simian hemorrhagic fever virus; Coronaviridae, such as, for example, Coronavirus, such as, for example, Avian infectious bronchitis virus, Avian infectious laryngotracheitis virus, Enteric coronavirus, Equine coronavirus, Group 1 species, such as, for example, Canine coronavirus, such as, for example, Canine enteric coronavirus (strain INSAVC-1), Canine enteric coronavirus (strain K378), Feline coronavirus, such as, for example, Feline enteric coronavirus (strain 79-1683), Feline infectious peritonitis virus (FIPV), Human coronavirus 229E, Porcine epidemic diarrhea virus, Transmissible gastroenteritis virus, such as, for example, Porcine respiratory coronavirus, Porcine transmissible gastroenteritis coronavirus, Group 2 species, such as, for example, Bovine coronavirus, Chicken enteric coronavirus, Human coronavirus OC43, Murine hepatitis virus, Porcine hemagglutinating encephalomyelitis virus, Puffinosis virus, Rat coronavirus, such as, for example, Rat coronavirus (strain 681), Rat sialodacryoadenitis coronavirus, Group 3 species, such as, for example, Turkey coronavirus, Human enteric coronavirus 4408, SARS coronavirus, Torovirus, such as, for example, Berne virus, Bovine torovirus, Breda virus, Human torovirus, Roniviridae; Okavirus such as, for example, Gill-associated virus, Yellow head virus, Nodaviridae, such as, for example, Alphanodavirus, such as, for example, Black beetle virus, Boolarra virus, Flock house virus, Nodamura virus, Pariacoto virus, Betanodavirus, such as, for example, Atlantic cod nervous necrosis virus, Atlantic halibut nodavirus, Barfin flounder nervous necrosis virus, Dicentrarchus labrax encephalitis virus, Dragon nervous necrosis virus, Epinephelus coioides nervous necrosis virus, Epinephelus tauvina nervous necrosis virus, Guppy nervous necrosis virus, Japanese flounder nervous necrosis virus, Malabaricus nervous necrosis virus, Red-spotted grouper nervous necrosis virus, Striped Jack nervous necrosis virus, Tiger puffer nervous necrosis virus, Umbrina cirrosa nodavirus, Picornaviridae, such as, for example, Aphthovirus, such as, for example, Equine rhinitis A virus, Foot-and-mouth disease virus, Cardiovirus, such as, for example, Encephalomyocarditis virus; Mengo virus, Porcine encephalomyocarditis virus, Theilovirus, such as, for example, Theiler's encephalomyelitis virus, Enterovirus, such as, for example, Bovine enterovirus, Coxsackievirus, Echovirus, Human echovirus 1, Human enterovirus A, Human enterovirus B, Human enterovirus C, Human enterovirus D, Human enterovirus E, Poliovirus, Porcine enterovirus A, Porcine enterovirus B, Sheep enterovirus, Erbovirus, such as, for example, Equine rhinitis B virus, Hepatovirus, such as, for example, Hepatitis A virus, such as, for example, Human hepatitis A virus, Simian hepatitis A virus, Kobuvirus, such as, for example, Aichi virus, Bovine kobuvirus, Parechovirus, such as, for example, Human parechovirus, Ljungan virus, Porcine enterovirus 11, Porcine enterovirus 2, Porcine enterovirus 3, Porcine enterovirus 4, Porcine enterovirus 5, Porcine enterovirus 6, Porcine enterovirus 7, Porcine enterovirus J1, Porcine enterovirus J10, Porcine enterovirus J2, Porcine enterovirus J3, Porcine enterovirus J4, Porcine enterovirus J5, Porcine enterovirus J6, Porcine enterovirus J7, Porcine enterovirus J9, Rhinovirus (common cold viruses), such as, for example, Equine rhinovirus 3, Human rhinovirus A, such as, for example; Human rhinovirus 11, Human rhinovirus 15, Human rhinovirus 16, Human rhinovirus 1A, Human rhinovirus 1B, Human rhinovirus 2, Human rhinovirus 21, Human rhinovirus 29, Human rhinovirus 36, Human rhinovirus 39, Human rhinovirus 49, Human rhinovirus 50, Human rhinovirus 58, Human rhinovirus 62, Human rhinovirus 65, Human rhinovirus 7, Human rhinovirus 85, Human rhinovirus 89, Human rhinovirus 9, Human rhinovirus B, such as, for example; Teschovirus, such as, for example, Human rhinovirus 14, Human rhinovirus 3, Human rhinovirus 72, Porcine teschovirus, unclassified Picornaviridae, such as, for example, Avian encephalomyelitis virus, Clethrionomys glareolus picornavirus, Maus-Elberfeld virus, Picornaviridae strain 62.3, Picornaviridae strain 62.4, Picornaviridae strain 62.8, Picornaviridae strain 62.9, Picornaviridae strain IG.26, Simian picornavirus 1, Simian picornavirus 10, Simian picornavirus 11, Simian picornavirus 12, Simian picornavirus 13, Simian picornavirus 15, Simian picornavirus 17, Simian picornavirus 18, Simian picornavirus 2, Simian picornavirus 3, Simian picornavirus 4, Simian picornavirus 5, Simian picornavirus 6, Simian picornavirus 7, Simian picornavirus 7', Simian picornavirus 8, Simian picornavirus 9, Simian picornavirus strain N125, Simian picornavirus strain N203, Tetraviridae, such as, for example, Betatetravirus, such as, for example, Nudaurelia capensis beta virus, Omegatetravirus, such as, for example, Nudaurelia capensis omega virus, unclassified Tetraviridae, such as, for example, Helicoverpa armigera stunt virus, Providence virus, Thosea asigna virus, Togaviridae, such as, for example, Alphavirus (arboviruses group A), such as, for example, BFV complex, such as, for example; Barmah Forest virus, EEEV complex, such as, for example, Eastern equine encephalitis virus, Igbo Ora virus, Karelian fever virus, Middelburg virus, NDUV complex, such as, for example, Ndumu virus, Salmon pancreas disease virus, Seal louse virus, SFV complex, such as, for example, Bebaru virus, Chikungunya virus, Getah virus, Mayaro virus, Me Tri virus, O'nyong-nyong virus, Ross River virus, Sagiyama virus, Semliki forest virus, Una virus, Sleeping disease virus, Trocara virus, VEEV complex, such as, for example, 71D1252 virus, 78V3531 virus, Ag80-663 virus, Bijou Bridge virus, Cabassou virus, Mucambo virus, Tonate virus, Pixuna virus, Venezuelan equine encephalitis virus, WEEV complex, such as, for example, Aura virus, Fort Morgan virus, Buggy Creek virus, Highlands J virus, Sindbis virus; such as, for example, Babanki virus, Kyzylagach virus, Ockelbo virus, Sindbis virus (strain HRSP), Sindbis virus (wild type SB derived from strain AR339), Sindbis-like virus, Sindbis-like virus YN87448, Western equine encephalomyelitis virus, Whataroa virus, Rubivirus, such as, for example, Rubella virus.

Preferably, the positive strand single-stranded RNA virus or nucleic acid thereof used to stimulate or activate the formation of the RNA complement of the recombinant RNA is a plant virus, preferably a Cowpea chlorotic mosaic virus (CCMV), a Brome mosaic bromovirus (BMV), a Lettuce mosaic virus, a Tobacco etch virus, a Tobacco vein mottle virus, a Pepper mottle virus, or a Tomato aspermy virus. More preferably, the virus is a CCMV or a BWMV. The RNA virus cannot be a Cucumber mosaic virus when the 3' UTR of the transgene is that of Lettuce mosaic virus. It is expected that many different species of positive strand single-stranded RNA virus or nucleic acid thereof can encode polypeptides (such as, for example, an RNA-dependent RNA polymerase) that comprise a replication complex that recognizes a 3' UTR of a recombinant RNA as described herein. Preferably, the virus or nucleic acid thereof used to stimulate or activate the formation of the RNA complement of the recombinant RNA can be the same virus as the source of the 3' UTR of the recombinant RNA or transgene.

The method as described herein, therefore, comprises providing a transgenic cell or organism comprising a recombinant DNA, the recombinant DNA comprising a promoter operably linked, in 5' to 3' direction, the complement of a coding sequence for a heterologous polypeptide, the complement of an IRES, and a 3' UTR of an RNA virus; infecting the cell or organism with a virus or a portion thereof, or transfecting the cell or organism with an RNA or a cDNA of an RNA virus or portion thereof, wherein the portion provides sequences encoding viral polypeptide components of a replication complex, such as, for example, an RNA-dependent RNA polymerase.

The kit as described herein comprises a DNA vector comprising, in the 5' to 3' direction, a promoter, at least one site for incorporation of coding sequence of a heterologous polypeptide in an antisense orientation, an anti-IRES, and a 3' UTR of a positive strand single-stranded RNA virus, and packaging. A user of the kit can, for example, incorporate coding sequence for a heterologous polypeptide into the DNA vector such that transcription of the vector would yield a transcript comprising, in the 5' to 3' direction, the complement of the coding sequence, the complement of the IRES, and the 3' UTR. The kit can further comprise a positive strand single-stranded RNA virus or nucleic acid thereof that, upon infection or transfection, would support the formation of an RNA complementary to the recombinant RNA. The kit can further comprise a host organism for growing the vector, such as, for example, transformation-competent *E. coli*. In some aspects, the kit can further comprise laboratory disposables such as, for example, plastic tubes and pipette tips. The kit can further comprise instructions and packaging.

EXAMPLES

Example 1

This example illustrates recombination of complementary copies of viral transgenes during viral replication.

Cowpea chlorotic mottle bromovirus (CCMV) was used initially to demonstrate that transgenic viral gene transcripts are available in the cytoplasm for recombination with a replicating virus (Greene and Allison, *Science* 263: 1423-1425, 1994). In these experiments, transgenic transcripts included part of the viral coat gene as well as a complete CCMV 3' UTR. However, when a portion or all of the 3' UTR was deleted from the transgenic viral gene transcript, viral recombination was below detection limits, suggesting that recombination of a transcript of a viral transgene requires the presence of an intact 3' UTR in the transcript. Without being limited by theory, the observations suggested that the presence of a complete 3' UTR enhances the stability of a transcript of the transgene in the cytoplasm, thereby prolonging the transcript's availability for recombination. These observations raise the possibility that the complete 3' UTR and its replication complex binding site may be recognized by a replication complex of a challenging virus, and a complementary copy of a transgenic transcript capable of contributing to recombination events may be synthesized in the cytoplasm. Recombination events could involve both an original transgenic transcript and its complementary copy, and could occur during either positive or negative strand synthesis.

Example 2

This example illustrates plasmid construction of vectors, including plasmids comprising part of a CCMV RNA3 gene 3a open reading frame (ORF) plus all or part of a CCMV RNA3 3' UTR.

Wild type CCMV RNA3 has a 3a gene ORF and a coat protein (CP) ORF (FIG. 2). A cDNA copy is maintained in plasmid pCC3TP4. A Not I restriction site was introduced near the 3' end of the CP gene ORF in plasmid pCC3AG1 as well as the viral transgenes in transgenic plants 3-57 and Δ69 (Greene and Allison, *Science* 263: 1423-1425, 1994; Greene and Allison, *Virology* 225: 231-234, 1996). Transgenic plant 3-57 was transformed with the 3' 2/3 of the CP ORF and the full-length 3' UTR. Transgenic plant Δ69 was transformed with the same viral gene, but the 3' UTR bears a a 69-nucleotide deletion at the 3' end. The negative sense RNA-specific primer RA83 (5'-AAGTGGATCCCCTC TTGTGCG-GCTGC-3' (SEQ ID NO: 1)) anneals at nucleotides 1519-1544, and was used for first strand cDNA synthesis and PCR. An additional primer RA84 (5'-ACTCCAAAGAGTTCT-TCCG-3' (SEQ ID NO: 2)) anneals at nucleotides 2072-2090, and was used for PCR.

Example 3

This example illustrates synthesis of a complementary copy of a viral transgene during viral replication, as well as detection of synthesis of a complementary copy of a viral transgene during viral replication.

A study was undertaken to determine if infection of a transgenic plant with either a wild type brome mosaic bromovirus (BMV) or a CCMV leads to synthesis of a complementary copy of a transcript of a viral transgene.

Three sets of plant materials were used in the study: non-transgenic *Nicotiana benthamiana*, clonally propagated transgenic *N. benthamiana* strain 3-57 and clonally propagated transgenic *N. benthamiana* strain Δ69. Strain 3-57 comprises a 694 nucleotide CCMV transgene comprising 451 3' nucleotides of the viral coat gene and a complete 243 nucleotide CCMV 3' UTR that is naturally contiguous with the viral coat protein gene (Greene and Allison, *Science* 263: 1423-1425, 1994). Transgenic strain Δ69 is similar but except that the terminal 69 nucleotides of the 3' UTR are deleted. Transgenic transcripts comprising a fragment of the transgenic coat gene used in both transgenic strains were distinguishable from wild type viral transcripts comprising coat gene by the alteration of nucleotides near the 3' end of the coat gene to create a Not I restriction site in each transgene (Greene and Allison, *Virology* 225: 231-234, 1996). Northern blot analysis indicated that both strains express transcripts of the transgenes.

BMV and CCMV are both positive strand single-stranded RNA viruses, no DNA stage. Although these viruses share tripartite genomic organization, they show only limited sequence identity. Source plants for BMV and CCMV were inoculated with BMV and CCMV transcripts. Transgenic plants used in the experiments were inoculated with leaf tissue extracts from the BMV- or CCMV-infected plants.

To define a period when virus replication was most active throughout the plant following basal leaf inoculation, digoxygenin-labeled probes specific for the 3' UTR of the genomic RNAs of BMV and CCMV, (HE1 and RA518(+), respectively) were used in dot blot assays to probe crude extracts derived from *N. benthamiana* plants inoculated with either BMV or CCMV. Hybridization indicated that 14 days post inoculation infections had spread to all leaves of 45-day old plants. However, attempts to detect minus strand copies of CCMV RNAs directly in total RNA extracted from non-transgenic plants in Northern blots were unsuccessful. Because of the possibility that an overwhelming amount of host and viral single strand RNA interfered with hybridization, single stranded RNA was removed from total RNA preparations by RNase treatment. Double-stranded RNA remaining after the RNase treatment was denatured and analyzed by Northern blot. In the resulting blots, minus strand CCMV RNA was detected by a $^{32}$P-labeled RNA probe, (RA518(−)) which was able to recognize the complementary copy of the 3' UTR of CCMV RNA. Using this probe, minus-sense genomic CCMV RNAs were detected in 0.5 to 1.0 gram samples of CCMV-infected transgenic *N. benthamiana* plant tissue at 14 days post infection (dpi). Probes were shown to be capable of detecting as little as 10 picogram (pg) of denatured plasmid DNA comprising CCMV sequence.

Figure 3:
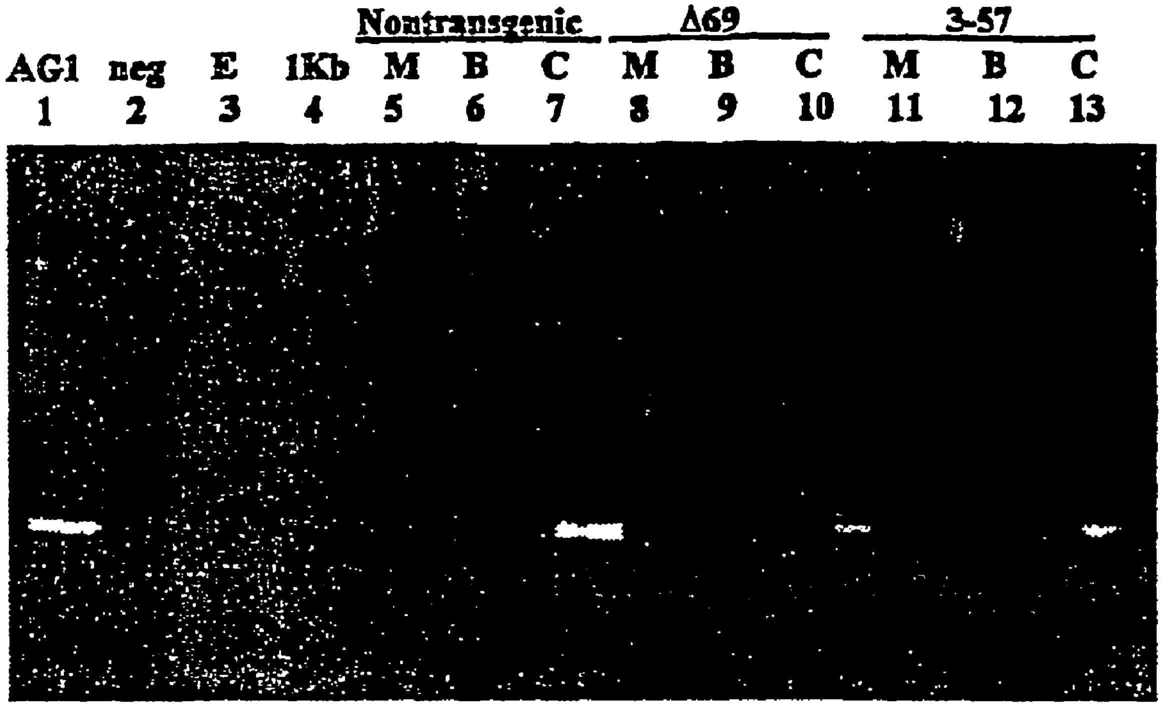
FIG. 3 illustrates agarose gel electrophoresis showing RT-PCR-amplified negative-sense Cowpea chlorotic mottle virus (CCMV) RNA3. Total RNA from virus infected or mock-inoculated transgenic and non-transgenic *N. benthamiana* plant tissue was treated with RNase-free DNase I to remove genomic DNA. A negative-sense CCMV RNA3-specific primer RA83 (5'-AAGTGGATCCCCTC TTGTGCG- GCTGC-3' (SEQ ID NO: 1)), which anneals at nucleotides 1519-1544, was used for first-strand cDNA synthesis. RA83 and an additional primer RA84 (5'-ACTCCAAAGAGTTCT-TCCG-3' (SEQ ID NO: 2)), which anneals at nucleotides 2072-2090, were used for PCR amplification. Lanes 5-7, 8-10, and 11-13 were from nontransgenic, transgenic Δ69, and 3-57 plants, respectively. Samples in lanes 5, 8 and 11 were mock-inoculated (M); lanes 6, 9 and 12 were inoculated with Brome mosaic virus (B): lanes 7, 10 and 13 were inoculated with CCMV (C). Lane 1 contains PCR product using 0.1 μg pCC3AG1 plasmid DNA. Lane 2 is a negative control of PCR in which water was added to the PCR mixture. Lane 3 is empty (E). Lane 4 comprises 1 kb size markers (Gibco BRL).

To determine whether a complementary copy of the transgenes was synthesized during virus infection, transgenic lines 3-57 and Δ69 were inoculated with either BMV or CCMV. At 14 dpi, RNA was subjected to analysis by a reverse transcription-polymerase chain reaction (RT-PCR) method (FIG. 3). In this procedure, total RNA from two grams of leaf tissues was extracted, and treated with RNase-free DNase I to remove the plant genomic DNA, including the chromosomal copy of the viral genome. A minus-strand CCMV RNA3-specific primer, "RA83," comprising the sequence 5'-AAGTGGATCCCCTC TTGTGCGGCTGC-3' (SEQ ID NO: 1), which anneals to nucleotides 1519-1544 of the transgenes was used for first-strand cDNA synthesis. PCR amplification employed RA83 as well as "RA84," which comprises the sequence 5'-ACTCCAAAGAGTTCTTCCG-3' (SEQ ID NO: 2). RA84 anneals to nucleotides 2072-2090 of the transgenes. The predicted size of an a fragment amplified by RT-PCR was 572 base pairs (bp). Analysis of RNA from plant tissue samples revealed that minus-strand RNA of the predicted size was synthesized in CCMV-infected plants of all strains tested, including 3-57, Δ69, and nontransgenic plants (FIG. 3). As shown in FIG. 3, lanes 7, 10 and 13, a minus-strand RNA was amplified in all the CCMV-infected 3-57, A69, and nontransgenic plants. A band of the predicted size was also present in the BMV-infected 3-57 transgenic plants (FIG. 3, lane 12). This minus-sense RNA was not observed in any mock-inoculated transgenic plants or in BMV-infected Δ69 or non-transgenic plants (FIG. 3, lanes 5, 6, 8, 9 and 11).

Figure 4:
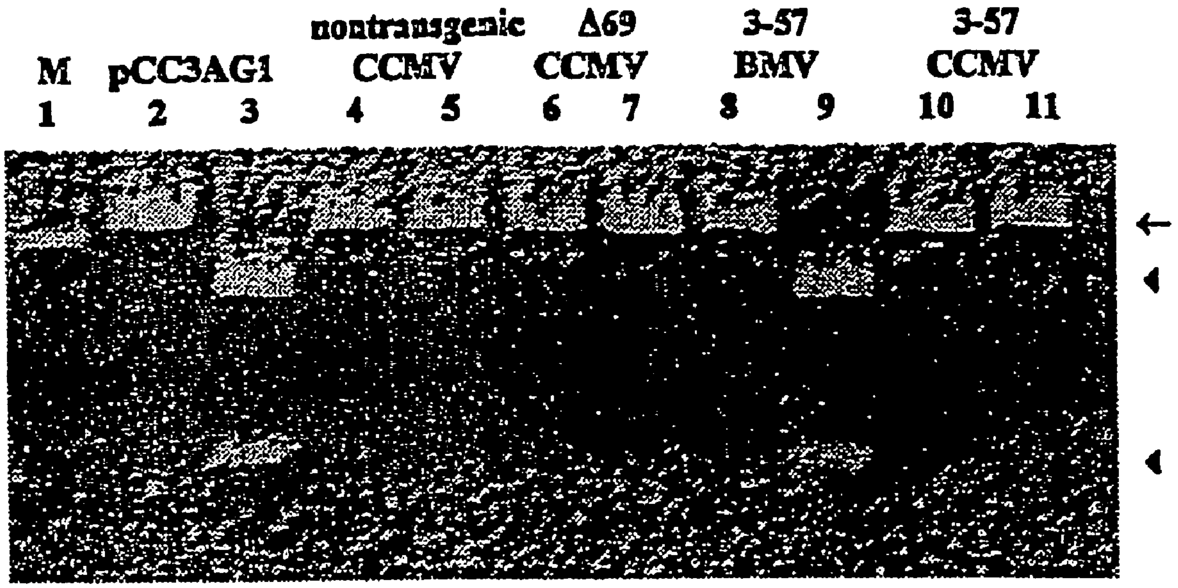
FIG. 4 illustrates an agarose gel showing Not I-digested RT-PCR products amplified from total RNA extracted from virus infected plant tissue. Lane 1 comprises a 1 kb size marker (Gibco BRL). Lanes 2-3 comprise PCR products amplified from pCC3AG1. Lanes 4-5 comprise RT-PCR-amplified products from CCMV-infected non-transgenic *N. benthamiana* plants. Lanes 6-7 comprise RT-PCR-amplified products from CCMV-infected Δ69 plants. Lanes 8-9 comprise RT-PCR-amplified products from BMV infected 3-57 plants. Lanes 10-11 comprise RT-PCR-amplified products from CCMV-infected 3-57 plants. RT-PCR products in lanes 2, 4, 6, 8 and 10 were not treated with Not I restriction enzyme. RT-PCR products in lanes 3, 5, 7, 9 and 11 were digested with Not I restriction enzyme. An arrow "←" indicates undigested fragments. An arrowhead "◄" indicates Not 1-digested fragments (in lanes 3, 9 and 11; note small digested bands in lane 11).

To determine if the 572 bp PCR products originated from transgene transcripts, PCR products were digested with Not 1. Because only the transgene product but not the wild-type CCMV inoculum comprises a Not I restriction site, a change in electrophoretic mobility is expected only from digestion of cDNAs of the trangenes. As shown in FIG. 4, lane 3, RT-PCR product of pCC3AG1 mutant containing the Not I site was completely cleaved by the Not I restriction enzyme, but that of wild type CCMV was not cleaved (FIG. 4, lane 7), indicating that the minus-strand CCMV RNA amplified in CCMV-infected Δ69 transgenic plants was from the wild type CCMV. The RT-PCR product of CCMV-infected transgenic 3-57 plants was partially cleaved by Not I (FIG. 4, lane 11), indicating that for CCMV-infected transgenic 3-57 plants, the minus-sense CCMV RNA3 which was amplified by RT-PCR was of two origins: both viral and transgene. For BMV-infected 3-57 transgenic plants, the RT-PCR product was completely cleaved by Not L No PCR fragment was present in the BMV-inoculated Δ69 plants (FIG. 3, lane 9). The data indicate that a full-length complementary copy of a transcript of a viral transgene is synthesized only when the 3' UTR of the viral transgene is intact. Thus the RT-PCR-amplified fragment was derived solely from a complementary copy of a viral transgene transcript. These data indicate that BMV recognized a replicase recognition and minus-strand initiation site on the CCMV transgene and synthesized a complementary copy. Although $F_1$ seedlings of 3-57 plants were used in these experiments, similar results were obtained when $F_0$ plant cuttings were used in repeated experiments.

These data demonstrate that the replication complex of either BMV or CCMV will recognize and synthesize a complementary copy of a CCMV transgene that contains a complete 3' UTR. Together with the findings of Teycheney et al. (*J. Gen. Virol.* 81: 1121-1126, 2000), the data demonstrate in several plant viral systems that inclusion of the replication complex binding site in a transgenic construct may lead to the synthesis of the transgene's complement.

Example 4

This example illustrates a prophetic example of expression of a transgene. In this prophetic example, a DNA transgene could comprise a CaMV 35S promoter operatively linked to a complementary copy of a sequence encoding barnase (a cell toxin; Leuchtenberger et al., *Nucleic Acid Res.* 29: E76, 2001), a complementary copy of an encephalomyocarditis virus IRES, and a 3' UTR of a Cowpea chlorotic mottle virus. Cells of a *Nicotiana benthamiana* plant harboring this transgene are expected to express an RNA comprising complementary copy of the sequence encoding barnase, a complementary copy of the encephalomyocarditis virus IRES, and the 3' UTR of cowpea chlorotic mottle virus. No barnase is expected to be detectable in any plant tissue prior to application of a stimulus. Upon infection of the plant with a virus such as a Cowpea chlorotic mottle virus or a Brome mosaic virus, a complementary copy of the recombinant RNA is expected to be produced. Because a complementary copy of the recombinant RNA is expected to comprise both the encephalomycocarditis virus IRES and a "sense" copy of the sequence encoding the barnase, it is expected that an infected cell will synthesize the barnase. Because cell death is expected to result from barnase expression, the virus is expected to be unable to replicate in infected cells, and the viral infection is expected to be unable to spread from cell to cell.

Example 5

This example illustrates a prophetic example of expression of a transgene. In this prophetic example, a DNA transgene could comprise a CaMV 35S promoter operatively linked to a complementary copy of a sequence encoding preproinsulin, a complementary copy of an encephalomyocarditis virus IRES, and a 3' UTR of a Cowpea chlorotic mottle virus. Cells of a *Nicotiana benthamiana* plant harboring this transgene are expected to express an RNA comprising a complementary copy of the sequence encoding preproinsulin, a complementary copy of the encephalomyocarditis virus IRES, and the 3' UTR of cowpea chlorotic mottle virus. No preproinsulin is expected to be detectable in any plant tissue prior to application of a stimulus. Upon infection of the plant with a virus such as a Cowpea chlorotic mottle virus or a Brome mosaic virus, a complementary copy of the recombinant RNA is expected to be produced. Because a complementary copy of the recombinant RNA is expected to comprise both the encephalomycocarditis virus IRES and a "sense" copy of the sequence encoding the preproinsulin, it is expected that an infected cell will synthesize the preproinsulin, and as the infection spreads throughout the plant, additional cells are expected to synthesize preproinsulin.

As various changes could be made in the above methods and compositions without departing from the scope of the invention, it is intended that all matter contained in the above description be interpreted as illustrative and not in a limiting sense.

All references cited in this specification are hereby incorporated by reference in their entirety. The discussion of the references herein is intended merely to summarize the assertions made by their authors and no admission is made that any reference constitutes prior art relevant to patentability. Applicant reserves the right to challenge the accuracy and pertinency of the cited references.

I claim:

1. A method of producing a heterologous polypeptide, the method comprising:

a) providing a transgenic plant or a transgenic plant cell comprising a recombinant DNA molecule comprising, in the 5' to 3' direction,
   i) a plant promoter;
   ii) a sequence complementary to a coding sequence for a heterologous polypeptide;
   iii) a sequence complementary to a plant virus internal ribosome entry site; and
   iv) a 3' UTR sequence having a sequence encoding a viral RNA replication initiation site;

b) growing the transgenic plant or transgenic plant cell;

c) producing an RNA transcript of the DNA sequence in the transgenic plant or the transgenic plant cell, the RNA transcript being a complementary RNA copy of the DNA sequence;

d) infecting the transgenic plant or the transgenic plant cell with an RNA nucleic acid encoding an RNA-dependent RNA polymerase operable to recognize the viral RNA replication initiation site and convert the RNA transcript produced by the transgenic plant or the transgenic plant cell to a translatable mRNA, the mRNA having a RNA sequence comprising, in the 5' to 3' direction:
   i) a sequence complementary to the 3' UTR sequence;
   ii) a coding sequence of the plant virus internal ribosome entry site; and
   iii) a coding sequence of the heterologous polypeptide; and e) translating the translatable mRNA in the transgenic plant or the transgenic plant cell to form the heterologous polypeptide.

2. The method of producing a heterologous polypeptide of claim 1, wherein the plant promoter is a selected from the group consisting of a constitutive promoter and an inducible promoter.

3. The method of producing a heterologous polypeptide of claim 2, wherein the constitutive promoter is a cauliflower mosaic virus 35S promoter.

4. The method of producing a heterologous polypeptide of claim 1, wherein the coding sequence for the heterologous polypeptide encodes a polypeptide selected from the group consisting of a hormone, an enzyme, a cell toxin, a viral polypeptide, a cell surface polypeptide, and an intracellular polypeptide.

5. The method of producing a heterologous polypeptide of claim 1, wherein the internal ribosome entry site is selected from the group consisting of a turnip mosaic potyvirus IRES, a tobamovirus IRES, and a hibiscus chlorotic ringspot virus IRES.

6. The method of producing a heterologous polypeptide of claim 1, wherein the sequence complementary to an internal ribosome entry site is a sequence complementary to a picornavirus internal ribosome entry site.

7. The method of producing a heterologous polypeptide of claim 1, wherein the 3' UTR sequence is obtained from a positive strand single-stranded RNA plant virus RNA with no DNA stage.

8. The method of producing a heterologous polypeptide of claim 1, further comprising a sequence complementary to an intron.

9. The method of producing a heterologous polypeptide of claim 1, wherein said DNA sequence further comprises a transcription termination signal sequence.

10. The method of producing a heterologous polypeptide of claim 1, wherein the transgenic plant is a dicotyledonous plant.

11. The method of producing a heterologous polypeptide of claim 10, wherein the dicotyledonous plant is a *Nicotiana* plant.

12. The method of producing a heterologous polypeptide of claim 11, wherein the *Nicotiana* plant is a *Nicotiana benthamiana* plant.

13. The method of producing a heterologous polypeptide of claim 1, wherein the infecting the transgenic plant or the transgenic plant cell for synthesis of an RNA complementary to an RNA transcript of the recombinant DNA comprises infecting the transgenic plant or the transgenic plant cell with a positive strand single-stranded RNA plant virus operable to recognize the viral RNA replication initiation site and convert the RNA transcript produced by the transgenic plant or the transgenic plant cell to a translatable mRNA.

14. The method of producing a heterologous polypeptide of claim 13, wherein the positive strand single-stranded RNA plant virus is a positive strand single-stranded RNA plant virus having no DNA stage.

15. The method of producing a heterologous polypeptide of claim 14, wherein the positive strand single-stranded RNA plant virus having no DNA stage is selected from the group consisting of a Bromovirus, a Tobacco etch virus, a Tobacco vein mottle virus, and a Pepper mottle virus.

16. The method of producing a heterologous polypeptide of claim 1, wherein the heterologous polypeptide produced in a cell infected with the RNA nucleic acid when compared as a molar ratio to the amount of the heterologous polypeptide produced in a cell not provided the RNA nucleic acid, ranges at least from about 50:1 to about 10,000:1.

17. The method of producing a heterologous polypeptide of claim 1, wherein said method of producing a heterologous polypeptide in a transgenic plant is used to confer disease resistance to a transgenic plant further comprising conferring resistance to subsequent infection from a second positive strand single-stranded RNA virus.

18. A recombinant DNA molecule comprising, in the 5' to 3' direction:

a) a plant promoter;

b) a sequence complementary to a coding sequence for a heterologous polypeptide;

c) a sequence complementary to a plant internal ribosome entry site; and d) a 3' UTR sequence comprising a DNA sequence of a 3' UTR RNA sequence of a positive strand single-stranded RNA plant virus.

19. The recombinant DNA molecule of claim 18, wherein the plant promoter is selected from the group consisting of a constitutive promoter and an inducible promoter.

20. The recombinant DNA molecule of claim 19, wherein the constitutive promoter is a cauliflower mosaic virus 35S promoter.

21. The recombinant DNA molecule of claim 18, wherein the coding sequence for the heterologous polypeptide encodes a polypeptide selected from the group consisting of a hormone, an enzyme, a cell toxin, a viral polypeptide, a cell surface polypeptide, and an intracellular polypeptide.

22. The recombinant DNA molecule of claim 18, wherein the sequence complementary to a plant internal ribosome entry site is a sequence complementary to a plant internal ribosome entry site (IRES) selected from the group consisting of a turnip mosaic potyvirus IRES, a tobamovirus IRES, and a hibiscus chlorotic ringspot virus IRES.

23. The recombinant DNA molecule of claim 18, wherein the sequence complementary to a plant internal ribosome entry site is a sequence complementary to a tobamovirus internal ribosome entry site.

24. The recombinant DNA molecule of claim 18, wherein the 3' UTR DNA sequence is a DNA copy of a positive strand single-stranded RNA plant virus RNA having no DNA stage.

25. The recombinant DNA molecule of claim 24, wherein the positive strand single-stranded RNA virus RNA having no DNA stage is a 3' UTR of a bromovirus.

26. The recombinant DNA molecule of claim 18, further comprising a sequence complementary to an intron.

27. The recombinant DNA molecule of claim 18, further comprising a transcription termination signal.

28. A transgenic plant comprising the recombinant DNA molecule of claim 18.

29. A transgenic plant cell of claim 28.

30. The transgenic plant of claim 28, wherein the transgenic plant is a transgenic dicotyledonous plant.

31. The transgenic dicotyledonous plant of claim 30, wherein the transgenic dicotyledonous plant is a transgenic *Nicotiana* plant.

32. Transgenic seed comprising the recombinant DNA molecule of claim 18.

33. A vector having at least one site for insertion of a recombinant DNA construct having inserted therein the recombinant DNA molecule of claim 18.

34. A vector according to claim 33, wherein the at least one site for insertion further comprises a recombination site.

35. A vector according to claim 34, wherein the recombination site is selected from the group consisting of a bacteriophage lambda att site and a topoisomerase I-based recombination site.

36. A vector according to claim 33, wherein the at least one site for insertion further comprises at least one restriction enzyme recognition site.

37. A vector according to claim 36, wherein the at least one restriction enzyme recognition site comprises a polylinker.

38. A recombinant RNA molecule comprising, in the 5' to 3' direction:

a) an RNA sequence comprising a sequence complementary to a coding sequence for a heterologous polypeptide;

b) a sequence complementary to an internal ribosome entry site; and c) a 3' UTR of a positive strand single-stranded RNA virus.

39. The recombinant RNA molecule of claim 38, wherein the coding sequence for a heterologous polypeptide encodes a polypeptide selected from the group consisting of a hormone, an enzyme, a cell toxin, a viral polypeptide, a cell surface polypeptide, and an intracellular polypeptide.

40. The recombinant RNA molecule of claim 38, wherein the sequence complementary to an internal ribosome entry site is a sequence complementary to an IRES selected from the group consisting of a picornavirus IRES, a foot-and-mouth disease virus IRES, an encephalomyocarditis virus IRES, a hepatitis A virus IRES, a hepatitis C virus IRES, a human rhinovirus IRES, a poliovirus IRES, a swine vesicular disease virus IRES, a turnip mosaic potyvirus IRES, a human fibroblast growth factor 2 mRNA IRES, a pestivirus IRES, a Leishmania RNA virus IRES, a Moloney murine leukemia virus IRES a human rhinovirus IRES, aphthovirus IRES, a human immunoglobulin heavy chain binding protein mRNA IRES, a *Drosophila* Antennapedia mRNA IRES, a human fibroblast growth factor 2 mRNA IRES, a hepatitis G virus IRES, a tobamovirus IRES, a vascular endothelial growth factor mRNA IRES, a Coxsackie B group virus IRES, a c-myc protooncogene mRNA IRES, a human MYT2 mRNA IRES, a human parechovirus type 1 virus IRES, a human parechovirus type 2 virus IRES, a eukaryotic initiation factor 4GI mRNA IRES, a Plautia stali intestine virus IRES, a Theiler's murine encephalomyelitis virus IRES, a bovine enterovirus IRES, a connexin 43 mRNA IRES, a homeodomain protein Gtx mRNA IRES, an AML1 transcription factor mRNA IRES, an NF-kappa B repressing factor mRNA IRES, an X-linked inhibitor of apoptosis mRNA IRES, a cricket paralysis virus RNA IRES, a p58(PITSLRE) protein kinase mRNA IRES, an ornithine decarboxylase mRNA IRES, a connexin-32 mRNA IRES, a bovine viral diarrhea virus IRES, an insulin-like growth factor I receptor mRNA IRES, a human immunodeficiency virus type 1 gag gene IRES, a classical swine fever virus IRES, a Kaposi's sarcoma-associated herpes virus IRES, a short IRES selected from a library of random oligonucleotides, a Jembrana disease virus IRES, an apoptotic protease-activating factor 1 mRNA IRES, a Rhopalosiphum padi virus IRES, a cationic amino acid transporter mRNA IRES, a human insulin-like growth factor 11 leader 2 mRNA IRES, a giardiavirus IRES, a Smad5 mRNA IRES, a porcine teschovirus-1 talfan IRES, a *Drosophila* Hairless mRNA IRES, an hSNM1 mRNA IRES, a Cbfa1/Runx2 mRNA IRES, an Epstein-Barr virus IRES, a hibiscus chlorotic ringspot virus IRES, a rat pituitary vasopressin V1b receptor mRNA IRES, and a human hsp70 mRNA IRES.

41. The recombinant RNA molecule of claim 38, wherein the sequence complementary to an internal ribosome entry site is a sequence complementary to a picornavirus internal ribosome entry site.

42. The recombinant RNA molecule of claim 38, wherein the 3' UTR of a positive strand single-stranded RNA virus is a 3' UTR of a positive strand single-stranded RNA virus having no DNA stage.

43. The recombinant RNA molecule of claim 42, wherein the 3' UTR of a positive strand single-stranded RNA virus having no DNA stage is a 3' UTR of a bromovirus.

44. The recombinant RNA molecule of claim 38, further comprising a sequence complementary to an intron.

45. A transgenic cell or transgenic plant comprising the recombinant RNA molecule of claim 38.

46. The transgenic cell of claim 45, wherein the transgenic cell is a transgenic plant cell.

47. The transgenic plant of claim 45, wherein the transgenic plant is a transgenic dicotyledonous plant.

48. The transgenic dicotyledonous plant of claim 47, wherein the transgenic dicotyledonous plant is a transgenic *Nicotiana* plant.

49. The transgenic *Nicotiana* plant of claim 48, wherein the transgenic *Nicotiana* plant is a transgenic *Nicotiana benthamiana* plant.

50. The method of producing a heterologous polypeptide of claim 1, wherein infecting the transgenic plant or the transgenic plant cell with an RNA nucleic acid comprises infecting the transgenic plant or the transgenic plant cell with a positive strand single-stranded RNA plant virus having a RNA genome operable to recognize and activate the viral RNA replication initiation site and convert the RNA transcript produced by the transgenic plant or transgenic plant cell to a translatable mRNA.

51. The method of producing a heterologous polypeptide of claim 1, wherein infecting the transgenic plant or the transgenic plant cell with an RNA nucleic acid comprises transfecting the transgenic plant or the transgenic plant cell with a RNA of a positive strand single-stranded virus operable to recognize and activate the viral RNA replication initiation site and convert the RNA transcript produced by the transgenic plant or transgenic plant cell to a translatable mRNA.

* * * * *

UNITED STATES PATENT AND TRADEMARK OFFICE

CERTIFICATE OF CORRECTION

PATENT NO. : 7,696,406 B2
APPLICATION NO. : 10/561720
DATED : April 13, 2010
INVENTOR(S) : Richard F. Allison It is certified that error appears in the above-identified patent and that said Letters Patent is hereby corrected as shown below:

Title Page, Item (56), References Cited, Other Publications, page 2, column 1, reference No. 10, “protecteed” should be --protected--.

Column 7, line 28, “viruses” should be --virus--.

Column 9, line 22, “an site” should be --att site--.

Column 10, line 22, “a-coding” should be --α-coding--.

Column 10, line 23, “a-IRES” should be --α-IRES--.

Column 12, line 39, “(CaMV) $^{35}$S” should be --(CaMV) 35S--.

Column 12, line 44, “NeIF4A10” should be --NeIF-4A10--.

Column 12, line 54, “CAMV” should be --CaMV--.

Column 12, line 55, “comprises” should be --comprise--.

Column 19, line 55, “mosaic, virus” should be --mosaic virus--.

Column 22, line 7, “italian” should be --Italian--.

Column 23, line 37, “chlorofic” should be --chlorotic--.

Column 27, line 44, “BWMV should be --BMV--.

Column 28, line 66, “bears a a” should be --bears a--.

Signed and Sealed this
Twenty-second Day of March, 2011

David J. Kappos
*Director of the United States Patent and Trademark Office*

Column 30, line 18, after “of”, delete “an”.

Column 30, line 26, “A69” should be --Δ69--.

Column 30, line 36, “trangenes” should be --transgenes--.

Column 30, line 49, “Not L” should be --Not I.--.

Column 31, line 17, “cowpea” should be --Cowpea--.

Column 32, line 10, “cowpea” should be --Cowpea--.

Column 42, line 36, Claim 2, after “is”, delete “a”.

Column 44, line 62, Claim 40, “rhinovirus IRES” should be --rhinovirus 14 IRES--.

Column 44, line 62, Claim 40, before “aphthovirus”, insert --an--.